United States Patent
Conrad et al.

(10) Patent No.: US 10,487,322 B2
(45) Date of Patent: Nov. 26, 2019

(54) ALKYLENE GLYCOLS AND POLYMERS AND COPOLYMERS THEREOF FOR DIRECT ISOLATION OF NUCLEIC ACID FROM EMBEDDED SAMPLES

(71) Applicant: Life Technologies Corporation, Carlsbad, CA (US)

(72) Inventors: Richard Conrad, Austin, TX (US); Marie Gonzalez, Austin, TX (US); Emily Zeringer, Buda, TX (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 0 days.

(21) Appl. No.: 15/829,469

(22) Filed: Dec. 1, 2017

(65) Prior Publication Data

US 2018/0087048 A1    Mar. 29, 2018

Related U.S. Application Data

(63) Continuation of application No. 13/307,788, filed on Nov. 30, 2011.

(60) Provisional application No. 61/418,242, filed on Nov. 30, 2010.

(51) Int. Cl.
    *C12Q 1/68* (2018.01)
    *C12N 15/10* (2006.01)
    *C12Q 1/6804* (2018.01)

(52) U.S. Cl.
    CPC ....... *C12N 15/1003* (2013.01); *C12Q 1/6804* (2013.01)

(58) Field of Classification Search
    USPC ......... 435/6.1, 6.11, 91.1; 436/94; 536/23.1, 536/24.3
    See application file for complete search history.

(56) References Cited

U.S. PATENT DOCUMENTS

| | | | |
|---|---|---|---|
| 4,994,200 A | 2/1991 | Disch | |
| 5,075,430 A | 12/1991 | Little et al. | |
| 5,234,809 A | 8/1993 | Boom et al. | |
| 5,288,627 A * | 2/1994 | Nielsen | C11D 3/38609 435/223 |
| 5,705,628 A | 1/1998 | Hawkins | |
| 6,027,945 A | 2/2000 | Smith et al. | |
| 6,469,159 B1 | 10/2002 | Belly et al. | |
| 7,157,416 B2 * | 1/2007 | Becker | C11D 3/38663 424/94.1 |
| 7,410,753 B2 | 8/2008 | Hopkins et al. | |
| 7,544,471 B2 | 6/2009 | Wang et al. | |
| 2003/0092045 A1 | 5/2003 | Nargessi et al. | |
| 2003/0162877 A1 * | 8/2003 | Chaiko | C08K 9/08 524/445 |
| 2005/0059024 A1 | 3/2005 | Conrad | |
| 2005/0059054 A1 | 3/2005 | Conrad et al. | |
| 2005/0123954 A1 | 6/2005 | Feldsine | |
| 2005/0208510 A1 | 9/2005 | Latham et al. | |
| 2008/0050746 A1 | 2/2008 | McMaster et al. | |
| 2009/0298129 A1 | 12/2009 | Spence et al. | |
| 2011/0098342 A1 * | 4/2011 | Ramadass | C12Q 1/6806 514/44 A |
| 2012/0149088 A1 | 6/2012 | Conrad et al. | |

FOREIGN PATENT DOCUMENTS

| WO | WO2002/046463 | 6/2002 |
|---|---|---|
| WO | WO2012075133 | 6/2012 |

OTHER PUBLICATIONS

Ghafoor et al., Characteristics of an extracellular protease isolated from Bacillus subtilis AG-1 and its performance in relation to detergent components. Annals of Microbiology, 59 (3), 559-563, Sep. 2009.*
Clayton et al., "In Situ Hybridization Using PEG-Embedded Tissue and Riboprobes: Increased Cellular Detail Coupled with High Sensitivity" *The Journal of Histochemistry and Cytochemistry*, vol. 37, No. 3, Mar. 1989, 389-393.
Gonzalez et al., "Thermostabilization of Cuburbita Ficifolia Protease in the Presence of Additives", *Biotechnology Letters*, vol. 14, No. 10, Oct. 1992, 919-924.
PCT/US2011/062631, International Search Report and Written Opinion, dated Feb. 2, 2012.
PCT/US2011/062631, International Preliminary Report on Patentability, dated Jun. 13, 2013.
Sakurai et al., "Solid Phase Synthesis of Peptides with Polyethylene Glycol-Modified Protease in Organic Solvents", *Biotechnology Letters*, vol. 12, No. 9, 1990, 685-688.
Slebos et al., "A Rapid and Simple Procedure for the Routine Detection of ras Point Mutations in Formalin-Fixed, Paraffin-Embedded Tissues", *Diagnostic Molecular Pathology*, vol. 1, No. 2, Jun. 1992, 136-141.
Smithson et al., "Polyethylene glycol embedding: a technique compatible with immunocytochemistry, enzyme histochemistry, histofluorescence and intracellular staining", *Journal of Neuroscience Methods*, vol. 7, No. 1, Jan. 1983, 27-41.
Wikipedia, "protease K", the free encyclopedia, printed Apr. 22, 2013.

* cited by examiner (Continued)

*Primary Examiner* — Frank W Lu

(57) ABSTRACT

Methods of directly isolating nucleic acid from an embedded biological sample are provided. An emulsified digest is generated in the presence of a thermostable protease, and an additive selected from an alkylene glycol, a poly(alkylene glycol), or a block copolymer having an average $M_n$ of 76 to 2900, or a salt or derivative or combination thereof. Nucleic acid is isolated directly from the emulsified digest. The methods eliminate the use of organic solvents such as xylene in a deparaffinization step prior to isolating nucleic acids from paraffin-embedded samples, for example.

11 Claims, 9 Drawing Sheets

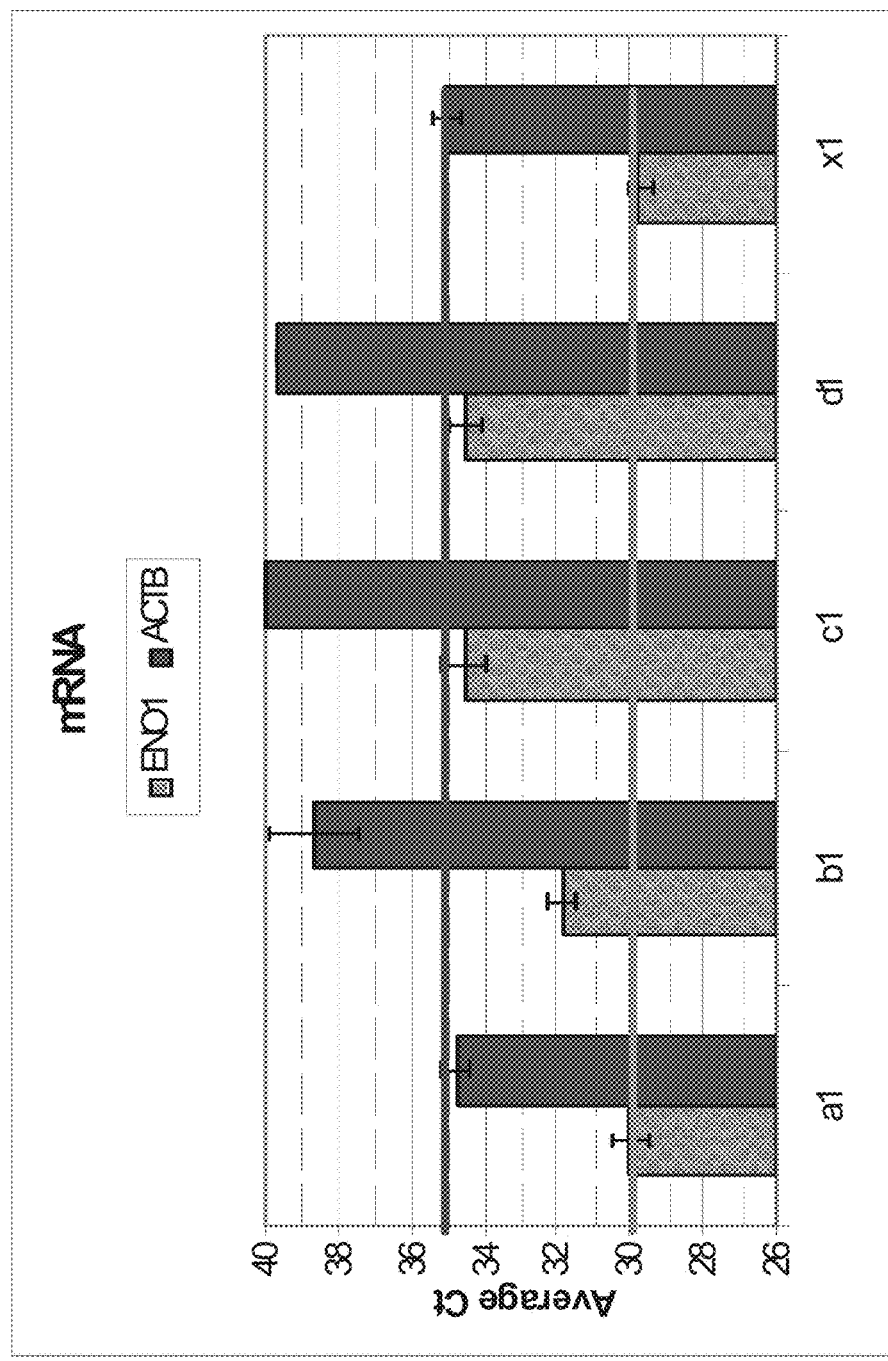

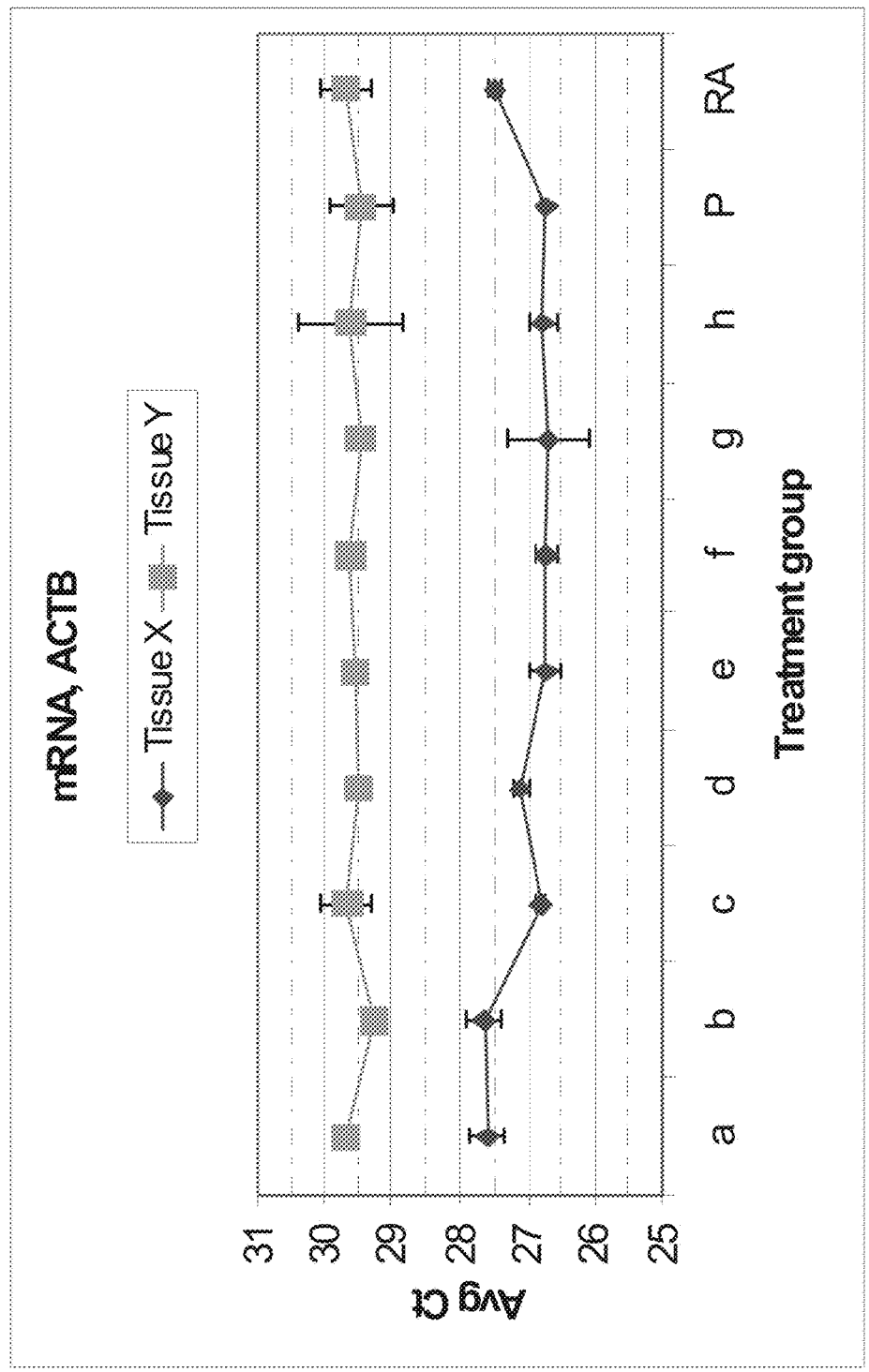

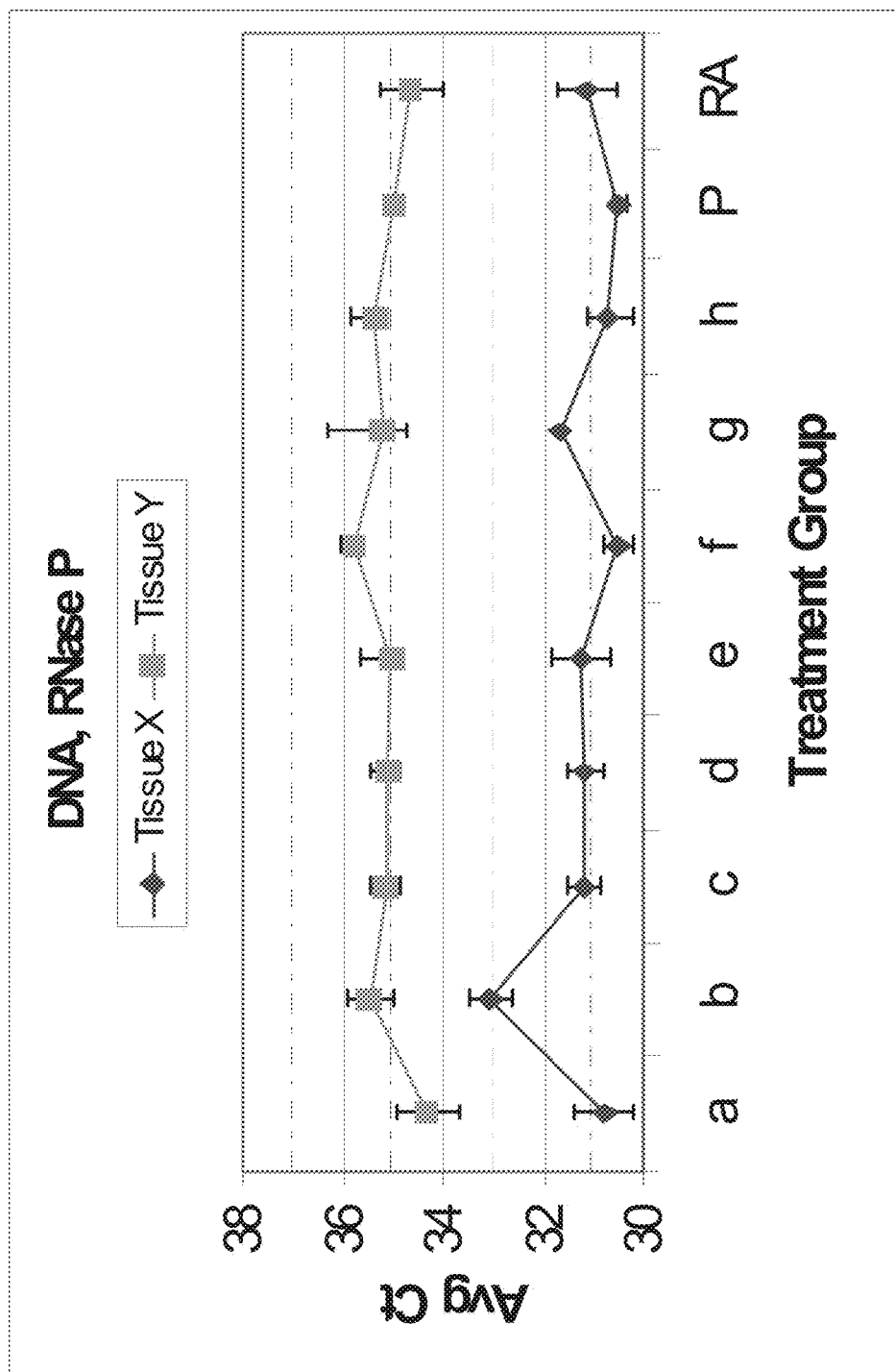

ALKYLENE GLYCOLS AND POLYMERS AND COPOLYMERS THEREOF FOR DIRECT ISOLATION OF NUCLEIC ACID FROM EMBEDDED SAMPLES

CROSS-REFERENCE TO RELATED APPLICATIONS

This application is a continuation application under 35 U.S.C. § 120 of U.S. application Ser. No. 13/307,788 filed Nov. 30, 2011, now abandoned, which application claims the benefit under 35 U.S.C. § 119(e) of U.S. Provisional Application No. 61/418,242 filed Nov. 30, 2010. The entire contents of the aforementioned applications are incorporated by reference herein.

This specification relates to methods and kits for directly isolating nucleic acid from an embedded biological sample. The methods eliminate the use of organic solvents such as xylene in a separate deparaffinization step prior to isolating nucleic acids from paraffin-embedded samples, for example.

BACKGROUND

Fixed biological samples are routinely impregnated and embedded in paraffin wax or paraffin blends to preserve them for later analysis. Nucleic acid isolation from these samples is usually performed after the paraffin wax or paraffin blend has been removed by extraction with organic solvents such as toluene, xylene, limonene, or other suitable solvent. These organic solvents are very volatile and require special processing such as use of ventilated hoods and special waste disposal. The use of these organic solvents increases the cost of analysis and exposure risk associated with each sample tested and has serious negative effects for the environment. Further, use of such organic solvents is not amendable to high throughput isolation and analytical methods.

Alternate methods provide for heating the paraffin embedded sample such that the paraffin melts and is physically separated from nucleic acid. See, for example, U.S. Published Patent Application No. 2008/0050746. U.S. Pat. No. 7,410,753 relates to heating a biological sample and a paraffin embedding media above the melting point of the paraffin embedding media, and rinsing with a paraffin embedding media-immiscible fluid in order to remove the heated paraffin embedding media from the biological sample, and replacing the paraffin embedding medium with a fixation solution.

Embodiments herein provide for in situ nucleic acid isolation from biological samples embedded in a hydrophobic matrix such as paraffin or a paraffin-blend. No separate step of removing embedding medium is used. Further, the embodiments presented herein are automation friendly and enable high throughput processing of said samples.

SUMMARY

Embodiments herein provide methods for isolation of nucleic acid from an embedded biological sample comprising contacting the embedded biological sample with a) a thermostable protease, and b) an additive comprising i) an alkylene glycol having an average $M_n$ of 76 to 2900, ii) a poly(alkylene glycol) having an average $M_n$ of 76 to 2900, iii) a copolymer having an average $M_n$ of 76 to 2900, iv) a salt of i), ii) or iii), v) a derivative of i), ii) or iii), or vi) any combination of i), ii) iii), iv) or v) under conditions to provide an emulsified digest; and isolating nucleic acid from the emulsified digest. The methods provide for direct isolation of nucleic acid or in situ isolation of nucleic acid, i.e., no physical separation of layers is used in methods herein and no organic solvent extraction of the embedding medium is used in methods herein.

In an embodiment, the additive comprises an alkylene glycol, or a salt or derivative or a combination thereof. The additive may comprise a combination of different alkylene glycols. In some embodiments, the additive comprises a propylene glycol, or a salt, a derivative, or a combination thereof. In some embodiments, the alkyl of the alkylene may be C3, C4, C5, C6, or more, or isomers thereof, such that the average $M_n$ of the alkylene glycol is from about 76 to about 2900.

In further embodiments, the additive comprises a poly (alkylene glycol), or a salt or derivative or a combination thereof, particularly a poly(ethylene glycol) or a poly(propylene glycol), or a salt or derivative or combination thereof. The poly(alkylene glycol) may comprise a combination of poly(alkylene glycols). In some embodiments, the alkyl of the poly(alkylene glycol) may be C2, C3, C4, C5, C6, or more, or isomers thereof, such that the average $M_n$ of the poly(alkylene glycol) is from about 76 to about 2900.

In other embodiments, the additive comprises a copolymer, or a salt or derivative or combination thereof. The copolymer may comprise an alternating copolymer, a periodic copolymer, a statistical copolymer, a random copolymer, a block copolymer, or a graft copolymer. In some embodiments, the copolymer comprises a block copolymer. In some embodiments, the block copolymer comprises a poly(alkylene-1 glycol)-block-poly(alkylene-2 glycol)-block-poly(alkylene-1 glycol), or a salt or derivative or combination thereof. In some embodiments, the alkyl of the poly(alkylene-1 glycol) and the poly(alkylene-2 glycol) may be C2, C3, C4, C5, C6, or more, or isomers thereof, such that the average $M_n$ of the block copolymer is from about 76 to about 2900. In such embodiments, alkylene-1 and alkylene-2 are different. In some embodiments, the block copolymer comprises poly(ethylene glycol)-block-poly(propylene glycol)-block-poly(ethylene glycol), or a salt or derivative or combination thereof. In other embodiments, the copolymer is a block copolymer and the block copolymer comprises poly(propylene glycol)-block-poly(ethylene glycol)-block-poly(propylene glycol), or a salt or derivative or combination thereof.

The embedded biological sample comprises an embedding medium which is also described as a hydrophobic matrix. The embedding medium, in some embodiments, comprises paraffin or a paraffin blend. In some embodiments, the embedded biological sample comprises a FFPE tissue sample.

Contacting the embedded biological sample with a thermostable protease and an additive under conditions to provide an emulsified digest includes, for example, heating the sample, the protease and the additive to provide an emulsified digest. In further embodiments, conditions comprise use of a mild chaotrope during the contacting step, or heating in the presence of the mild chaotrope. Nucleic acids of the emulsified digest may be directly isolated therefrom using any method known by one of ordinary skill in the art of nucleic acid isolation. In particular, nucleic acid isolation comprises contacting the emulsified digest with a solid support under conditions wherein nucleic acid binds to the solid support; and eluting the nucleic acid from the solid support to provide eluted nucleic acid.

In certain embodiments, the nucleic acid is DNA and isolating DNA comprises a further step of contacting the eluted nucleic acid with a ribonuclease to form a ribonuclease digest, contacting the ribonuclease digest with a solid support under conditions wherein DNA binds to the solid support; and eluting the DNA from the solid support.

In certain embodiments, the nucleic acid is RNA and isolating RNA comprises a further step of contacting the eluted nucleic acid with a deoxyribonuclease to form a deoxyribonuclease digest, contacting the deoxyribonuclease digest with a solid support under conditions wherein RNA binds to the solid support, and eluting the RNA from the solid support.

Kits comprising a) a thermostable protease, and b) an additive comprising i) an alkylene glycol having an average $M_n$ of 76 to 2900, ii) a poly(alkylene glycol) having an average $M_n$ of 76 to 2900, iii) a copolymer having an average $M_n$ of 76 to 2900, iv) a salt of i), ii) or iii), v) a derivative of i), ii) or iii), or vi) any combination of i), ii) iii), iv) or v) as set forth above are also embodiments provided herein. In some embodiments the kits further comprise a digestion buffer, and/or a mild chaotrope. In some embodiments, kits comprise components for reverse transcription of RNA or for quantitation of DNA or cDNA by PCR or qPCR. In some embodiments, the kits include instructions for isolation of nucleic acid from an embedded biological sample.

Further embodiments include use of any of the methods described herein in the isolating of nucleic acid from an embedded biological sample, particularly an FFPE sample.

These and other features of the present disclosure will become more apparent from the description herein.

BRIEF DESCRIPTION OF THE DRAWINGS

The skilled artisan will understand that the drawings, described below, are for illustration purposes only. The drawings are not intended to limit the scope of the present teachings in any way.

FIG. 2A-FIG. 2C provide RNA yield (FIG. 2A), qRT-PCR results for two mRNA targets (FIG. 2B), and qRT-PCR results for two miRNA targets (FIG. 2C) using direct nucleic acid isolation from clinical FFPE block samples in the presence of various additives as described in Example 4.

FIG. 3A-FIG. 3E provide RNA yield (FIG. 3A), DNA yield (FIG. 3B), qRT-PCR results for mRNA target ACTB (FIG. 3C), qPCR results for DNA target RNase P (FIG. 3D) and qRT-PCR results for miRNA target Let-7a (FIG. 3E) for two different types of tissue of clinical FFPE block samples in the presence of various additives as described in Example 5.

DETAILED DESCRIPTION

Figure 1:
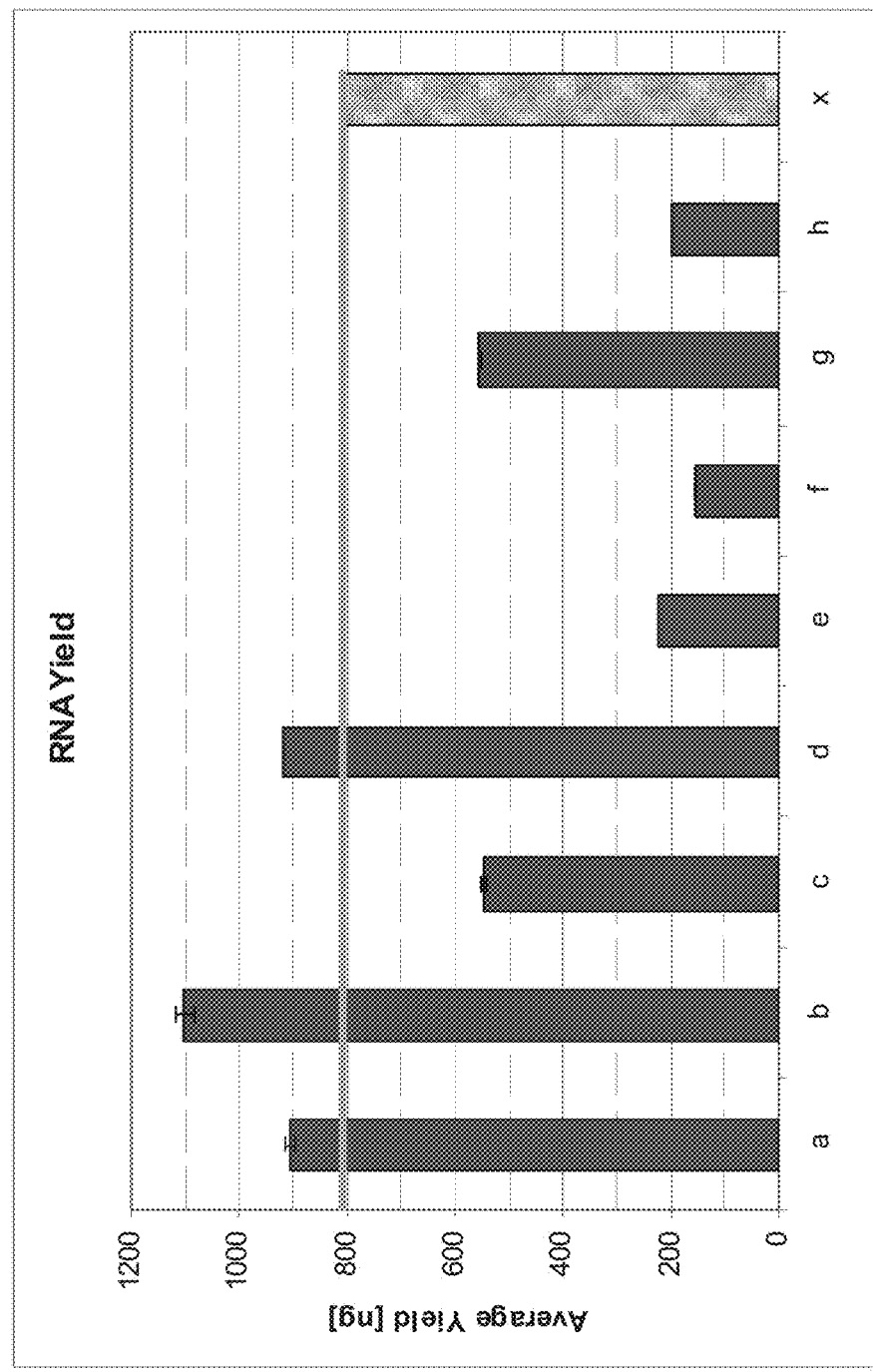
FIG. 1 provides yield of RNA using direct nucleic acid isolation from clinical FFPE block samples in the presence of various additives as described in Example 3.

It is to be understood that both the foregoing general description and the following detailed description are exemplary and explanatory only and are not intended to limit the scope of the current teachings. In this application, the use of the singular includes the plural unless specifically stated otherwise. Also, the use of "comprise", "contain", and "include", or modifications of those root words, for example but not limited to, "comprises", "contained", and "including", are not intended to be limiting. Use of "or" means "and/or" unless stated otherwise. The term "and/or" means that the terms before and after can be taken together or separately. For illustration purposes, but not as a limitation, "X and/or Y" can mean "X" or "Y" or "X and Y".

Whenever a range of values is provided herein, the range is meant to include the starting value and the ending value and any value or value range therebetween unless otherwise specifically stated. For example, "from 0.2 to 0.5" means 0.2, 0.3, 0.4, 0.5; ranges therebetween such as 0.2-0.3, 0.3-0.4, 0.2-0.4; increments there between such as 0.25, 0.35, 0.225, 0.335, 0.49; increment ranges there between such as 0.26-0.39; and the like.

The section headings used herein are for organizational purposes only and are not to be construed as limiting the subject matter described in any way. All literature and similar materials cited in this application including, but not limited to, patents, patent applications, articles, books, treatises, and internet web pages, regardless of the format of such literature and similar materials, are expressly incorporated by reference in their entirety for any purpose. In the event that one or more of the incorporated literature and similar materials defines or uses a term in such a way that it contradicts that term's definition in this application, this application controls. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Methods provided herein allow the direct isolation of nucleic acid from embedded biological samples without prior removal of the embedding medium. For example, for a biological sample embedded in paraffin, the method provides an emulsified digest thereof that includes paraffin, the biological sample, a thermostable protease and an additive. The emulsified digest is used directly in a step of nucleic acid isolation. Therefore, the isolation of nucleic acid is a direct isolation or an in situ isolation. The methods are carried out under conditions to provide the emulsified digest, which conditions include presence of a mild chaotrope and heating. Such conditions allow the paraffin to be emulsified so that nucleic acid isolation is carried out in the presence of the emulsified digest. Thus, the methods eliminate the need for a deparaffinization step prior to isolating nucleic acids from paraffin-embedded samples. Thus, use of organic solvents such as xylene, benzene, toluene, ethylbenzene, limonene, octane, or mixtures thereof is eliminated.

Thus, an exemplary method includes contacting an embedded biological sample with a) a thermostable protease, and b) an additive comprising i) an alkylene glycol having an average $M_n$ of 76 to 2900, ii) a poly(alkylene glycol) having an average $M_n$ of 76 to 2900, iii) a copolymer having an average $M_n$ of 76 to 2900, iv) a salt of i), ii) or iii), v) a derivative of i), ii) or iii), or vi) any combination of i), ii) iii), iv) or v), in a digestion buffer for 15-60 minutes at a temperature of about 60° C., followed by an additional 15-30 minutes at 80° C. to provide an emulsified digest. The emulsified digest is used for in situ isolation of nucleic acids using methods known to one of ordinary skill in the nucleic acid art. For example, aqueous or alcoholic solutions for isolation of nucleic acids are added directly to the emulsified digest. The term "contacting" will be understood to have its plain and ordinary meaning to refer to the coming together of at least the embedded biological sample, the thermostable protease and the additive. The term will further be understood to encompass the terms "incubating," "exposing," "immersing" or "mixing."

In some embodiments, a binding solution is added directly to the emulsified digest and a bead-based nucleic acid extraction method is performed directly on the digest. In some embodiments, a solution is added to precipitate nucleic acids of the emulsified digest for further use or purification. In a bead-based procedure, for example, a mixture of binding buffer and isopropanol is added to the emulsified digest and thoroughly mixed, and either NANO-MAG-D® magnetic beads or Dynal MYONE™ silane beads were added. The standard protocol for the MAG-MAX™ Express-96 Magnetic Particle Processor is then followed for washing and elution.

Embedded Biological Sample: Embodiments of methods herein can be used for isolation of nucleic acid from biological samples that have been embedded with a hydrophobic matrix (an embedding medium) that is emulsifiable using an additive under conditions presented herein. Embedded samples generally are preserved or archived in the form of formalin-fixed paraffin-embedded samples (FFPE samples). The term "FFPE" refers to tissues or cells that have been treated by exposure to formalin and subsequently soaked thoroughly in a hydrophobic matrix such as paraffin or a paraffin blend so that the paraffin or paraffin blend has infiltrated the tissues or cells. Such samples are typically sliced into 5 to 10 micron-sized sections using a microtome for subsequent analysis.

Typically, the embedding medium for clinical samples is paraffin which refers to a waxy solid mixture of hydrocarbons at ambient temperature. The term paraffin is a term used synonymously with "alkane", indicating hydrocarbons with the general formula $C_nH_{2n+2}$. Paraffin wax refers to a mixture of alkanes that falls within the $20 \leq n \leq 40$ range; they are generally solid at room temperature. Paraffin blends include further materials that may enhance properties of the paraffin in embedding procedures. As used herein, the term "paraffin" includes paraffin wax and paraffin blend type embedding media (e.g., PARAPLAST® Media, PARAPLAST® Plus Media, PARAPLAST® X-tra Media, POLYFIN™ Embedding Medium, Paramat Embedding Medium, Paramat Extra Embedding Medium, for example). Older clinical embedded samples have been found preserved in beeswax which is comprised of fatty acid esters with long chain alcohols. Such a medium is considered a hydrophobic matrix as used herein.

Exposure to a fixative generally occurs prior to the embedding process. Chemical fixatives preserve tissue from degradation and assist in maintaining the structure of the cell and of sub-cellular components such as cell organelles (e.g., nucleus, endoplasmic reticulum, mitochondria). The most common fixative for FFPE samples is neutral buffered formalin (4% formaldehyde in phosphate buffered saline). The main effect of aldehyde fixatives is the crosslinking of groups in proteins and nucleic acids through the formation of $CH_2$ (methylene) linkage, in the case of formaldehyde, or by $C_5H_{10}$ cross-links in the case of glutaraldehyde. RNA or DNA obtained from formalin-fixed paraffin-embedded samples typically contains nucleotide-to-nucleotide and nucleotide-to-protein cross-links, base modifications and other chemical modifications that affect the integrity of the nucleic acid. For example, the reaction between formaldehyde and nucleotides forms a methylene bridge between amino groups of two nucleotides. This process, while preserving the structural integrity of the cells and tissue, can damage the biological functionality of proteins and nucleic acids.

The biological sample may comprise, for example, a forensic sample, a diagnostic sample such as a biopsy sample, or an investigational sample such as, for example, a tissue sample from a plant or animal, or a sample from a culture of a microorganism such as a eukaryotic microorganism, for example, a yeast. A biopsy sample may be a surgically-removed sample such as a fine needle aspirate, a core biopsy or a needle biopsy, or any tissue sample removed from a body for analysis. Tissues samples may comprise tissue of the brain, head, neck, gastrointestinal tract, lung, liver, pancreas, breast, testis, uterus, bladder, kidney, heart or skin, but is not limited to such tissues. The biological sample can comprise a tissue slice present on a histology slide. The biological sample can comprise both eukaryotic cells and prokaryotic cells. The eukaryotic cell can be from any eukaryotic organism including, but not limited to, a protozoa, a fungus, a plant, an animal, or a human. The animal and/or human cells can be hematopoietic cells. The animal and/or human cells can be cancer cells and/or infected cells. The cells can be tissue culture cells which, in some embodiments, may be used as a mimic for the corresponding tissue.

Thermostable Protease: As used herein, a "thermostable protease," is a protease that can be heated to moderate temperatures without losing efficacy. The term "thermostable" includes proteases isolated from thermostable as well as thermophilic organisms, or mutants or variants thereof. A "thermostable protease" includes, for example, proteinase K, thermolysin, protease S, thermitase, pre-Taq™ protease, or pyrolysin, for example. The amount of protease used in conditions to provide an emulsified digest is an effective amount to achieve a proteolytic digest of cells in a biological sample. The concentration of the protease can be about, at least about, or at most about 0.1, 0.2, 0.5, 1, 1.5, 2, 2.5, 3, 3.5 4, 4.5, 5, 10, 15, 20, 25, 50, 100, 125, 150, 175, 200, 300, 400, 500, 600, 700, 800, 900, 1000, 1100, 1200, 1300, 1400, or 1500 µg/ml or any range therein. Mutants or variants of a protease may be engineered or naturally occurring, and retain at least some of the desired enzymatic activity. Protocols for measuring enzymatic activity using an appropriate assay are known to one of ordinary skill in the art.

Embodiments herein provide for unexpectedly short digestion times when proteinase K is used in the presence of the additive. Without being bound by theory, the additive appears to be particularly effective at providing access by the enzyme to protein substrate in the biological sample.

Additives: An additive, as used herein, comprises i) an alkylene glycol having an average $M_n$ of 76 to 2900, ii) a poly(alkylene glycol) having an average $M_n$ of 76 to 2900, iii) a copolymer having an average $M_n$ of 76 to 2900, iv) a salt of i), ii) or iii), v) a derivative of i), ii) or iii), or vi) any combination of i), ii) iii), iv) or v). In some embodiments, the alkyl of the alkylene may be C2, C3, C4, C5, C6, or more, or isomers thereof, such that the average $M_n$ of the alkylene glycol or poly(alkylene glycol) or copolymer is from about 76 to about 2900. In some embodiments of alkylene glycol, the alkylene is other than ethylene.

Monomers of a copolymer, similarly, may be alkylene glycol, or a poly(alkylene glycol) and the alkyl of the alkylene is as above. In some embodiments, monomers of a copolymer may be regularly alternating (alternating copolymers), arranged in a repeating sequence (periodic copolymers), arranged according to known statistical rules (statistical copolymers), a truly random copolymer, have two or more homopolymer subunits linked by covalent bonds (block copolymers, e.g., diblock copolymers, triblock copolymers, triblock terpolymers), or may contain side chains that have a different composition or configuration than the main chain (graft or grafted copolymers).

In some embodiments, additives, as used herein, generally are liquid at ambient temperature. In some embodiments, the number average molecular weight ($M_n$) of additives herein is from about 76 to about 2900. $M_n$ represents the ordinary arithmetic mean or average of the molecular weights of the individual macromolecules. $M_n$ is determined by measuring the molecular weight of n polymer molecules, summing the weights, and dividing by n. In some embodiments, the $M_n$ of additives is between about 200 and about 2500, including but not limited to, 200, 400, 425, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, or 2000. In some embodiments, the additive has a $M_n$ of about 76, 400, 425, 1000, 1100, 1200, 1900, or 2000.

The additive may have a branched structure. The additive may be a derivative of an additive having substituent groups that allow the additive to function in isolation of nucleic acid from an embedded sample as described herein. Individual end-group substituents of an additive include, independently, substituents containing oxygen such as hydroxyl, aldehyde, or carboxyl; nitrogen such as amine, amide, aminoalkyl such as aminopropyl, or nitro; phosphorous such as phosphonic; or sulfur such as sulfonic, thiol or sulfhydryl, for example. Additives may be present in a salt form.

In some embodiments, the additive comprises poly(ethylene glycol) $M_n$ 200, $M_n$ 400, or $M_n$ 1000; poly(propylene glycol) $M_n$ 76.1, $M_n$ 400, $M_n$ 425, $M_n$ 1000, or $M_n$ 1200; poly(ethylene glycol)-block-poly(propylene glycol)-block-poly(ethylene glycol) $M_n$ ~1100, $M_n$ 1900, or $M_n$ 2000; or a poly(propylene glycol)-block-poly(ethylene glycol)-block-poly(propylene glycol) $M_n$ 2000, for example.

The additive is present during protease digestion of the embedded biological sample at a concentration of about 5% to 75% v/v, or about 5% to 60% v/v, or about 10% to 50% v/v, or about 15% to 50% v/v or about 5, 10, 15, 20, 25, 30, 35, 40, 45 or 50% v/v or any range in between.

Conditions to Provide an Emulsified Digest: Conditions to provide an emulsified digest include an amount of time, a temperature and buffer conditions in the presence of a chaotrope so that embedding medium is emulsified and cells are digested when an embedded biological sample is in contact with a protease and an additive as described herein. A digest results when a cell is lysed or its integrity is disrupted. Such conditions may vary depending on the size of the sample, the type of sample, the buffer, the time and the temperature.

The amount of time that an embedded biological sample is contacted to form an emulsified digest can be a few minutes to overnight, about 5 minutes to an hour, about 10 minutes to 45 minutes or about 30 minutes. It is contemplated that the amount of time may be about, at least about or at most about 5, 10, 15, 20, 25, 30, 35, 40, 45, 50, 55 minutes and/or 1, 2, 3, 4, 5, 6, 7, 8, 9, 10, 11, 12, 13, 14, 15, 16, 17, 18, 19, 20, 21, 22, 23, 24, or more hours, or any range therein.

The temperature at which an embedded biological sample is contacted to form an emulsified digest is a temperature at which the protease is active and the embedding medium is emulsified. The embedded biological sample is contacted to form an emulsified digest at temperatures that include, or are at least or at most about 35, 40, 45, 50, 55, 60, 65, 70, 75, 80, 85, 90° C. or any range therein. In some embodiments, the temperature is between about 40° C. and about 65° C., or between about 50° C. and about 60° C. Such temperatures may or may not be maintained during the entire contacting period.

In embodiments of the invention, the buffer in the digestion buffer is TrisCl, which may be in the buffer at a concentration of about, at least about, or at most about 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 225, 250, 275, 300, 350, 400, 450, 500, 600, 700, 800, 900, 1000 mM or any range therein. Although it is contemplated that other buffers may be employed as well.

The pH of the digestion buffer, or of the buffer component of the digestion buffer, or of the digestion buffer with the sample is between about 6.5 and 9.5, though it can be about, about at least, or about at most 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5 or any range therein.

In some embodiments, the digestion buffer contains a detergent. Detergents may be ionic or nonionic. In some embodiments, the detergent comprises one or more of N-lauroyl sarcosine, deoxycholate, CTAB, deoxycholate and sodium dodecyl sulfate (SDS). The ionic detergent SDS is specifically contemplated for use in digestion buffers of the invention. The concentration of the detergent in the buffer may be about, at least about, or at most about 0.1%, 0.2%, 0.3%, 0.4%, 0.5%, 0.6%, 0.7%, 0.8%, 0.9%, 1.0%, 1.5%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, 10.0% or any range therein. It is contemplated that the concentration of the detergent can be up to an amount that allows the detergent to be soluble in the buffer.

In further embodiments, it is specifically contemplated that the digestion buffer includes a mild chaotrope such as urea or formamide. In some embodiments, a digestion buffer includes a mild chaotrope at concentrations of about or at most about 0.1, 0.2, 0.5, 0.75, 1.0, 1.25, 1.5, 1.75, 2.0, 2.25, 2.5, 3.0, 3.5. or 4.0 M or more, or any range therein.

Digestion buffers can include a salt such as sodium chloride or sodium citrate, for example. Components of a digestion buffer can include other compounds that chemically or enzymatically disrupt components of a cell. A digestion buffer may include one or more of such components. Methods and compositions of the invention will also be understood to exclude compounds or limit their amount that result in fragmented or truncated RNA or DNA molecules. In a specific embodiment, the digestion buffer includes 2% SDS, 0.5 M urea, 200 mM TrisCl, pH 8, and 25 mM NaCitrate, pH 7.3.

Components used in the contacting step of methods herein may be added in a concentrated form or they may be provided in kits in a concentrated form. The components may be 2×, 3×, 4×, 5×, 10×, or 20×, for example.

The term "emulsified" refers to the dispersion, suspension, or solubilization of the embedding medium of the biological sample into an emulsified digest that includes the biological sample, protease and additive. The emulsified digest is in the form of fine, uniformly distributed droplets or particles.

Nucleic Acid Isolation: The emulsified digest is used directly for isolation of nucleic acids. Either or both RNA and DNA can be directly isolated from emulsified digests. The term "RNA" includes, for example, mRNA and its precursors, and non-coding RNA (ncRNA) including, but not limited to, rRNA, tRNA, micro RNAs (miRNA), short interfering RNAs (siRNA), small temporal RNAs (stRNA) or short nuclear RNAs (snRNA). The term "DNA" refers to deoxyribonucleic acid in its various forms as understood in the art, such as genomic DNA, cDNA, isolated nucleic acid molecules, vector DNA, and chromosomal DNA.

Isolation, as used herein, means removal of any contaminant from nucleic acid in any amount from the normal milieu of an embedded biological sample, thereby accomplishing a degree of isolation of the nucleic acid. Methods for isolating nucleic acid are well known in the art and may include any of a variety of techniques such as binding to a solid support such as glass fiber filters or magnetic beads or by alcohol fractionation, for example.

Procedures for isolation of RNA molecules, including microRNA and siRNA molecules are described in U.S. Published Patent Application No. 2005/0059024 to Conrad filed Sep. 19, 2003, related to the MIRVANA™ RNA isolation kits (Ambion, Austin Tex.). Procedures for RNA isolation from paraffin embedded tissue are described in U.S. Published Patent Application No. 2005/0059054 to Conrad et al. filed Jul. 26, 2004 related to the RECOVER-ALL® kit (Ambion), which kit was used herein to provide controls for effective nucleic acid isolation. Procedures of U.S. Published Patent Application No. 2005/0059054 may be used for nucleic acid isolation embodiments herein. However, the xylene deparaffinization step can be eliminated.

U.S. patent application Ser. No. 10/955,974 filed Sep. 30, 2004 (now U.S. Pat. No. 8,426,126) to Latham et al. teaches use of dextran-coated magnetic particles for isolation of either RNA or DNA. Said document is incorporated by reference herein in its entirety and cited particularly for nucleic acid isolation methods related to the use of NANOMAG® Dextran (Plain) and NANOMAG®-D(SO3H) magnetic beads supplied by Micromod (Germany), and BIOMAG® Dextran-Coated Charcoal and BIOMAG®Plus Dextran magnetic beads supplied by Polysciences, Inc. Because the methods of U.S. Pat. No. 8,426,126 provide for purification of both RNA and DNA, and, further, both small and large nucleic acid fragments, the use of such dextran-coated magnetic particles has applicability in essentially any context in which polynucleotide separation is desired.

Some nucleic acid techniques involve isolation of nucleic acids and fragments thereof using glass, silica, zeolite, or diatomaceous earth such as in U.S. Pat. Nos. 5,075,430 or 5,234,809. Methods may be used in a form with filters or columns, or as magnetically responsive particles (magnetic particles) to expedite separations. For example, U.S. Pat. No. 6,027,945 relates to purification of RNA and DNA from silica magnetic beads. U.S. Pat. No. 5,705,628 relates to carboxy-coated magnetic particles can be used to isolate DNA.

U.S. Patent Application Publication 2003/0092045 relates to use of cellulose particles or cellulose paper in the isolation and purification of nucleic acids such as DNA. Long chain carbohydrate molecules have been used to precipitate nucleic acids. For example, dextran and glycogen have been used as co-precipitants for DNA. Polyethyleneglycol (PEG), in combination with appropriate salt concentrations, induces nucleic acid precipitation.

In some embodiments, binding polynucleotides to polymer-modified magnetic microparticles such as dextran-coated magnetic beads, carboxy-coated or derivatized magnetic beads, either as is, or having a functional group-coated surface (e.g., a carboxy or sulfonic acid group-coated surface) comprises adjusting a salt concentration and the concentration of an organic solvent of the binding solution to a concentration of each suitable for binding polynucleotides reversibly onto the surface of the magnetic particles. Suitable salts may include guanidinium isothiocyanate (GITC), guanidinium hydrochloride, sodium chloride (NaCl), sodium citrate (Na citrate), sodium acetate (Na acetate), sodium perchlorate ($NaClO_4$), lithium chloride (LiCl), barium chloride ($BaCl_2$), potassium chloride (KCl), calcium chloride ($CaCl_2$), magnesium chloride ($MgCl_2$) and cesium chloride (CeCl). Generally, GITC is used. Other solutes, such as urea and thiourea may be combined therein. Suitable organic solvents may include methanol, ethanol, propanol, isopropanol, butanol, pentanol, acetone, or dimethylsulfoxide. Preferred solvents are ethanol, propanol, isopropanol, and dimethylsulfoxide. A sufficient quantity of a salt and a sufficient concentration of organic solvent are combined with the combination of magnetic microparticles and polynucleotide-containing solution to produce a final salt concentration of from about 0.5M to about 2.0M and a final organic solvent concentration of from about 20% to about 70%. At appropriate concentrations of the two, polynucleotides bind to the surface of the microparticles. The binding of the polynucleotides to the magnetic microparticles is rapid; it is generally complete within 2 min or less.

In one embodiment, the magnetic microparticles with bound polynucleotides are washed with a suitable wash buffer solution before separating the polynucleotides from the polymer microparticles by washing with an elution buffer. A suitable wash buffer solution has several characteristics and more than one type of wash buffer may be used. First, the wash buffer solution must have a sufficiently high concentration of salts and/or organic solvent such that the polynucleotides bound to the magnetic microparticles do not elute from of the microparticles, but remain bound to the microparticles. Suitable salt concentrations are about 0.5 M to 5.0 M, about 2 M or about 1 M, in the presence of 20 to 50% organic solvent. A wash solution may also include organic solvent without salt, at concentrations are greater than about 50% and preferably about 80%. The buffer solution is chosen so that impurities that are bound to the polynucleotides or microparticles are dissolved. The probability that this might occur is increased by using two wash solutions that differ in their composition. The pH and solute composition and concentration of the buffer solution can be varied according to the type of impurities which are expected to be present. The magnetic microparticles can be washed as often as required to remove the desired impurities. However, the number of washings is preferably limited to two or three in order to minimize loss of yield of the bound polynucleotide, and/or the particles themselves. When the microparticles are used in excess, RNA yields are typically 80% or greater after washing with a wash buffer and eluting with an elution buffer.

In some embodiments, both the binding buffer and the first wash include a detergent. Detergents may be ionic, which include anionic and cationic detergents, or nonionic. Examples of nonionic detergents include triton, such as the TRITON® X series (TRITON® X-100, TRITON® X-100R, TRITON® X-114, TRITON® X-450, TRITON® X-450R), octyl glucoside, polyoxyethylene(9)dodecyl ether, digitonin, IGEPAL CA630, n-octyl-beta-D-glucopyranoside (betaOG), n-dodecyl-beta, C12E07, TWEEN® 20, TWEEN® 80, polidocanol, n-dodecyl beta-D-maltoside (DDM), NP-40, C12E8 (octaethylene glycol n-dodecyl monoether), hexaethyleneglycol mono-n-tetradecyl ether (C14E06), octyl-beta-thioglucopyranoside (octyl thioglucoside, OTG), emulgen, and polyoxyethylene 10 lauryl ether (C12E10). Examples of ionic detergents (anionic or cationic) include deoxycholate, sodium dodecyl sulfate (SDS), N-lauryl sarcosine, and cetyltrimethylammoniumbromide (CTAB). The ionic detergent N-lauryl sarcosine (sarkosyl) is specifically contemplated for use in solutions herein. The concentration of the detergent in the buffer or a wash may be about, at least about, or at most about 0.05%, 0.1%, 0.2%, 0.3%, 0.4%, 0.5%, 0.6%, 0.7%, 0.8%, 0.9%, 1.0%, 2%, 3%, 4%, 5% or any range therein. It is contemplated that the concentration of the detergent can be up to an amount that allows the detergent to be soluble.

Temperature does not appear to be critical in the binding or washing steps of isolation of DNA or RNA of embodiments herein. In some embodiments, ambient temperature is preferred, but any temperature above the freezing point of water and below the boiling point of water may be used.

In other isolation embodiments using glass fiber filters, for example, isolation of RNA from the emulsified digest comprises use of a solution comprising alcohol for precipitation of RNA. The alcohol solution can be about, be at least about, or be at most about 5, 10, 15, 20, 25, 30, 35, 40, 45, 50, 55, 60, 65, 70, 75, 80, 85, 90, 95, 100% alcohol, or any range therein. In certain embodiments, it is added to a digest to make the digest have a concentration of alcohol of about, at least about, or at most about 5, 10, 15, 20, 25, 30, 33, 35, 40, 45, 50, 55, 60, 65, 70, 75, 80, 85, 90%, or any range therein. In specific embodiments, the amount of alcohol added to a digest renders it with an alcohol concentration of about 33%, 35%, 40%, 45%, 50%, 55%, 60%, 62%, 65%, or any range therein. Alcohols include, but are not limited to, ethanol, propanol, isopropanol, butanol, and methanol. Ethanol or isopropanol are specifically contemplated for use in aspects of the invention. Methods and composition for isolating small RNA molecules can be obtained from U.S. application Ser. No. 10/667,126, filed Sep. 19, 2003 (U.S. 2005/0059024) which document is hereby incorporated by reference.

The emulsified digest also could be extracted using phenol/chloroform for isolating nucleic acid as known by one of ordinary skill in the art. In such embodiments, equal amounts of 1) the digest and 2) phenol and/or chloroform are mixed.

In some embodiments, other compounds can be added to the digest for isolation procedures. In particular embodiments, a salt is added to the digest in addition to an alcohol. The salt may be any salt, though in certain embodiments, the salt is guanidinium or sodium, or a combination of both. The amount of salt added to the digest can render the concentration of one or more salts in the mixture to be about, at least about, or at most about 0.1, 0.2, 0.5, 0.75, 1.0, 1.25, 1.5, 1.75, 2.0, 2.5, 3.0, 3.5 M or more, or any range therein. In some embodiments, the salt is a sodium salt such as sodium acetate, sodium chloride, or sodium citrate. In certain embodiments, guanidinium is added to the digest to provide a concentration of guanidinium between about 0.5 and about 3 M. Consequently, the amount of guanidinium added to the digest provides a concentration of guanidinium that is about, at least about, or at most about 0.1, 0.2, 0.5, 1.0, 1.5, 2.0, 2.5, 3.0 M, or any range derivable therein.

Extraction of RNA from the digest may further include using a mineral support. In some methods of the invention, a digest that may or may not have been mixed with an alcohol or non-alcohol organic solvent solution is applied to a mineral support and the RNA is eluted from the support. Mineral supports include supports involving silica. In some embodiments, the silica is glass. Supports include, but are not limited to, columns and filters. In further embodiments, the mineral support is a glass fiber filter or column.

Alternatively, in some embodiments, isolation of RNA from the digest can include a non-silica support. The support may include non-reactive materials, that is, materials that do not react chemically with the RNA to be isolated or extracted. Such materials include polymers or nonpolymers with electronegative groups. In some embodiments, the material is or has polyacrylate, polyacrylonitrile, polyvinylchloride, methacrylate, and/or methyl methacrylate.

Thus, some embodiments include adding an alcohol solution to the digest, contacting the resultant mixture with a mineral support, and eluting the RNA from the mineral support with an elution solution. The mineral support may be washed 1, 2, 3, 4, 5 or more times after applying the mixture. Wash solutions include, in some embodiments, an alcohol, and in some cases, it also includes a salt. In further embodiments, the solution contains an alcohol concentration of about or at least about 50, 55, 60, 65, 70, 75, 80, 85, 90, 95%. In specific embodiments, the alcohol is ethanol. In additional embodiments, the salt concentration in the wash solution is about or is at least about 0.1, 0.2, 0.5, 1.0, 1.5, 2.0 M or more, or any range therein. Washes can be performed at a temperature that is about or is at least about 15, 20, 25, 30, 35, 40, 45, 50, 55, 60, 65, 70, 75, 80, 85, 90, 95, or 100° C., or any range derivable therein, including at an ambient temperature.

RNA can be eluted from a mineral support with an elution solution. In some embodiments, the elution solution is water. In some embodiments, the elution solution includes Tris-EDTA. The concentration of EDTA in an elution solution is between about 0.01 mM to about 1.0 mM or between about 0.05 mM and about 0.5 mM. In specific embodiments, the concentration of EDTA in the elution solution is about 0.1 mM. The elution solution may comprise a salt such as NaCl, Na citrate, Na acetate, KCl, $CaCl_2$, $MgCl_2$, for example. A salt may be present in the elution solution at a concentration of 0.05, 0.1, 0.2, 0.5, 1.0, 1.5, 2.0 mM or more, or any range therein. The elution solution and/or the mineral support when elution solution is applied may be at room temperature or it may be heated to a temperature between about 80° C. and about 100° C. In some embodiments, the temperature is about or is at least about 15, 20, 25, 30, 35, 40, 45, 50, 55, 60, 65, 70, 75, 80, 85, 90, 95, 100° C., or any range derivable therein.

After nucleic acid is isolated, individual or specific molecules and/or pools of molecules (as well as the entire population of isolated nucleic acid) can be subject to additional reactions and/or assays. In some cases, these reactions and/or assays involve amplification of the RNA or of a DNA molecule. The DNA molecule may be generated from the RNA. For example, RT-PCR may be employed to generate molecules that can be characterized.

Nucleic acid obtained from embedded biological samples using methods herein may be analyzed or quantitated by various methods known to one of ordinary skill in the nucleic acid art. RNA may be quantitated using qRT-PCR and DNA may be quantitated using qPCR. Nucleic acid may be quantitated or analyzed using gel electrophoresis, chromatography, UV spectroscopy, or fluorescence-based assays, for example. Nucleic acid may also be analyzed using an electrophoretic procedure that employs a capillary electrophoresis system (e.g., the Caliper RNA 6000 LabChip™ Kit and the Agilent 2100™ Bioanalyzer) or using microarray technology.

Commercially available instruments or kits for nucleic acid isolation include the following from Life Technologies (Carlsbad Calif.): IPREP™ Purification Instrument, CHARGESWITCH® Direct 96 gDNA Kits, CHARGESWITCH® EasyPlex, CHARGESWITCH®-Pro Plasmid Miniprep Kit, NA Purification & Quantification—DNAZOL®, GENECATCHER™ Magnetic Beads, TRIZOL® reagent, PURELINK™ RNA mini kit, MAGMAX™ nucleic acid isolation kits, MIRVANA™ nucleic acid isolation kits, DYNABEADS® DNA DIRECT™ isolation kits, DYNABEADS® mRNA DIRECT™ isolation kits, and DYNABEADS®MYONE™ Silane isolation kits. The following are from Promega (Madison Wis.): RELIAPREP™, WIZARD® and MAXWELL® gDNA purification kits; MAXWELL® 16 Total RNA Purification Kit; PolyATtract System 1000, PUREYIELD™ RNA Midiprep, SV Total RNA Isolation. The following are from Qiagen (Hilden Germany): QIAAMP™, QIASYMPHONY™, FLEXIGENE™, EZ1™, MAGATTRACT™, AND RNEASY™ nucleic acid isolation kits.

Other methods that may be employed use products known in the art such as RNAzol (Gibco BRL), TriReagent™ (Molecular Science), Qiagen's RNeasy™ Total RNA Isolation kit (Qiagen), Quickprep™ Total RNA Extraction kit (Amersham Bioscience) or any other manufactured protocol for isolation of RNA. Other methods of RNA extraction include but are not limited to, the guanidine thiocyanate and cesium trifluoroacetate (CSTFA) method, the guanidinium hydrochloride method, or the lithium chloride—SDS—urea method. See Sambrook et al. (2000); Maniatis et al. (1989); Ausubel et al. (1994), for example of methods of RNA extraction.

The present methods and kits may be employed for high throughput processing of embedded biological samples, particularly archived FFPE samples. Those samples associated with long term phenotypic data are of particular interest for discovery of biomarkers with diagnostic implications. The markers can be used for diagnosis, prognosis, typing, and/or staging of disease. Markers can include DNA or RNA markers and/or expression levels.

Kits: A "kit," as used herein, refers to a combination of at least some items for performing a method for direct isolation of nucleic acid from an embedded biological sample. Embodiments of kits comprise, for example, a thermostable protease and an additive comprising an alkylene glycol, a poly(alkylene glycol), or a copolymer having a number average molecular weight ($M_n$) of 76 to 2900, or a salt or derivative or combination thereof as described herein. In some embodiments of kits, the additive comprises an alkylene glycol, a combination of alkylene glycols, or a salt or derivative thereof, particularly a propylene glycol, or a salt or derivative or combination thereof. In further embodiments, the additive comprises a poly(alkylene glycol), a combination of poly(alkylene glycols), or a salt or derivative or combination thereof, particularly a poly(ethylene glycol) or a poly(propylene glycol), or a salt or derivative or combination thereof.

In further kit embodiments, the additive comprises a copolymer, or a salt or derivative or combination thereof. The copolymer may comprise an alternating copolymer, a periodic copolymer, a statistical copolymer, a random copolymer, a block copolymer, or a graft copolymer. In particular, the copolymer comprises a block copolymer of different poly(alkylene) glycols. In some embodiments, the block copolymer comprises poly(ethylene glycol)-block-poly(propylene glycol)-block-poly(ethylene glycol), or a salt or derivative or combination thereof. In another embodiment, the copolymer is a block copolymer and the block copolymer comprises poly(propylene glycol)-block-poly(ethylene glycol)-block-poly(propylene glycol), or a salt or derivative or combination thereof.

Certain kit embodiments comprise a "thermostable protease" such as, for example, proteinase K, thermolysin, protease S, thermitase, pre-Taq™ protease, or pyrolysin.

Kit embodiments may further comprise a digestion buffer, a detergent and/or a chaotrope as described above. In certain embodiments, the kit includes a binding buffer for binding to a solid support. Certain kit embodiments comprise a solid support such as a filter, column, or magnetic beads such as NANOMAG-D® magnetic beads or Dynal MYONE™ silane beads, carboxy-coated magnetic beads, a wash buffer, or an elution buffer. In certain embodiments for DNA isolation, the kit includes a ribonuclease to remove RNA, or a deoxyribonuclease inhibitor for protecting DNA against degradation. Such reagents are DNase-free. In certain other embodiments for RNA isolation, the kit includes a deoxyribonuclease to remove DNA, or a ribonuclease inhibitor for protecting RNA against degradation. Such reagents are RNase-free.

Embodiments of kits can further comprise RNA or a DNA control nucleic acid, reagents for isolating nucleic acid, reagents for reverse transcribing RNA including reverse transcriptase, reagents for amplifying DNA or cDNA including polymerase, deoxyribonucleotides dATP, dCTP, dGTP, or dTTP, or reagents for generating RNA including ribonucleotides rATP, rCTP, rGTP, rUTP, aminoallyl-rUTP, or biotin-rUTP.

Kits can include, for example, a control set of oligonucleotide probes, a control target nucleic acid, primers suitable for reverse transcription and first strand and second strand DNA synthesis to produce a target amplicon, a detector probe, a thermostable DNA-dependent DNA polymerase and free deoxyribonucleotide triphosphates. In some embodiments, the enzyme comprising reverse transcriptase activity and thermostable DNA-dependent DNA polymerase activity is one and the same enzyme.

The container means of the kits will generally include at least one vial, test tube, flask, bottle, syringe or other packaging means, into which a component can be placed, and in some embodiments, suitably aliquoted. Where more than one component is included in the kit (they can be packaged together), the kit also will generally contain at least one second, third or other additional container into which the additional components can be separately placed. However, various combinations of components can be packaged in a container means. The kits of the present teachings also will typically include a means for containing the reagent containers in close confinement for commercial sale. Such containers can include injection or blow-molded plastic containers into which the desired container means are retained. When the components of the kit are provided in one and/or more liquid solutions, the liquid solution comprises an aqueous solution that may be a sterile aqueous solution.

In certain embodiments, at least one kit component is provided as dried powder(s). When reagents and/or components are provided as a dry powder, the powder can be reconstituted by the addition of a suitable solvent. In certain embodiments, the solvent is provided in another container means. Kits may also comprise an additional container means for containing a sterile buffer and/or other diluent.

A kit may also include instructions for employing the kit components as well as the use of any other reagent not included in the kit. Instructions can include variations that can be implemented. Any embodiments discussed with respect to compositions and/or methods of embodiments herein, as well as any embodiments in the examples, are specifically contemplated as being part of a kit. Reagents for fixing tissue such as formalin, formaldehyde, or paraformaldehyde, and reagents for embedding tissue such as a paraffin wax or a paraffin blend may also be comprised in a kit.

Embodiments of the present teachings can be further understood in light of the following examples, which should not be construed as limiting the scope of the present teachings in any way.

EXAMPLE 1: Direct Isolation of Nucleic Acids from FFPE Clinical Samples

In the following examples, RNA (including miRNA) and DNA were isolated directly from FFPE samples without using xylene or ethanol extractions (or any other organic solvent extraction) of the paraffin. Additives were discovered to provide sufficient emulsification of paraffin such that digestion of tissue samples occurred in the presence of paraffin. No physical separation of paraffin was needed in isolations provided herein.

Additives examined for use in emulsifying paraffin included various detergents, alkylene glycols, polyalkylene glycols and various block copolymers. Table 1 provides ingredients of compositions used in nucleic acid isolations.

Human clinical FFPE blocks were of unknown tissue type, roughly 18-20 years old, and were obtained from a local hospital (Austin, Tex.). While the tissue types were unknown, visual inspection, based for example on the dispersity or granularity of the tissue, determined that different types of tissue were represented by the blocks. Rat samples (~6 months old) were obtained from Pel-Freez® Biologicals (Rogers, Ark.) and had been collected, fixed and embedded into FFPE blocks by the supplier.

Ten micron tissue sections were cut from the blocks. Control and test sections came from the same block. As a control for isolation procedures herein, one 10 µm section was used for isolation of RNA or DNA using the RECOVERALL™ Total Nucleic Acid Isolation Kit for FFPE (Applied Biosystems, cat#AM1975) including the deparaffinization using xylene and alcohol and the glass fiber filter recovery of nucleic acid.

For studies of additives used in isolation procedures herein, a 96-well deep well plate was prepared and one 10 µm section of tissue was placed in each well. Digestion Buffer (150 µl, see Table 1) was added and the tissue was pushed down into the liquid. Protease (4 µl, see Table 1) was added followed by 30 µl of an additive (from Table 1). The plate was covered with an optical cover. For RNA isolation, the sample was incubated at 60° C. (in a water bath) for 45 min followed by incubation at 80° C. for 30 min (also in a water bath). For DNA isolation, the sample was incubated at 60° C. (in a water bath) for 45-55 min followed by incubation at 80° C. for 30 min (also in a water bath). After the

TABLE 1

| Component | Composition |
|---|---|
| Digestion Buffer | 2% SDS |
| | 0.5M Urea |
| | 200 mM Tris-Cl, pH 8 |
| | 25 mM Sodium Citrate, pH 7.3 |
| Binding Buffer | 2.5M Guanidine thiocyanate |
| | 0.5% N-lauryl sarcosine |
| | 100 mM Sodium Citrate, pH 7 |
| Wash Solution 1 | 1.25M Guanidine thiocyanate |
| | 0.125% N-lauryl sarcosine |
| | 25 mM Sodium Citrate, pH 7 |
| | 50% Isopropanol |
| Wash Solution 2 | 2 mM Tris-Cl, pH 7 |
| | 0.2 mM EDTA |
| | 10 mM Potassium Chloride |
| | 80% Ethanol |
| Proteinase K | 50 mg/ml Proteinase K in storage buffer |
| Additives | Poly(ethylene glycol); $M_n$ 200; Sigma Aldrich, cat#P3015 |
| | Poly(ethylene glycol); $M_n$ 400; Aldrich, cat#202398 |
| | Poly(ethylene glycol); $M_n$ 1000; Aldrich, cat#P3515 |
| | Brij 30 |
| | Brij 35P |
| | Brij 56 |
| | Brij 76 |
| | Poly(ethylene glycol)-block-poly(propylene glycol)-block-poly(ethylene glycol); $M_n$ ~1100; Aldrich, cat#435406 |
| | Poly(ethylene glycol)-block-poly(propylene glycol)-block-poly(ethylene glycol); $M_n$ 1900; Aldrich, cat#435414 |
| | Poly(ethylene glycol)-block-poly(propylene glycol)-block-poly(ethylene glycol); $M_n$ 2000; Aldrich, cat#435422 |
| | Poly(propylene glycol)-block-poly(ethylene glycol)-block-poly(propylene glycol); $M_n$ 2000; Aldrich, cat #435473 |
| | Poly(propylene glycol); $M_n$ 76.1; Aldrich, cat# W294004 |
| | Poly(propylene glycol); $M_n$ 400; Aldrich, cat#81350 |
| | Poly(propylene glycol); $M_n$ 425; Aldrich, cat #202304 |
| | Poly(propylene glycol); $M_n$ 1000; Aldrich cat#202320 |
| | Poly(propylene glycol) $M_n$ 1200; Aldrich cat#81370 |
| DNase | TURBO ™DNase, 20 U/ul (Applied Biosystems) |
| RNase | RPA grade RNase A, 1 mg/ml |
| 1X DNase Buffer | 10 mM Tris-Cl, pH 7.5 |
| | 10 mM Magnesium Chloride |
| | 0.5 mM Calcium Chloride |
| | 0.25M Sodium Chloride |
| Elution Buffer | 0.2 mM Sodium Citrate (pH 7) |
| | 1 mM Potassium Chloride | incubation was complete, the plate was tapped to collect liquid from the cover and then 620 µl of binding buffer master mix was added to each well (200 µl of binding buffer combined with 420 µl 100% isopropanol in a separate container).

The plate was spun for ~5 s (pop-spin) and was cooled for 5 min at room temperature. While the samples were cooling, the automated instrument (MAGMAX™ Express-96 Magnetic Particle Processor, Applied Biosystems) was prepared according to the supplied protocol. Nucleic acid binding beads (20 µl; NANOMAG®-D plain, Micromod, Germany,) was added to each well, the MagMAX™ instrument was loaded as prompted, and the protocol started.

The MagMAX™ instrument protocol included the following sequence of steps: the sample was mixed with binding buffer mix and beads for 3 min, the beads were collected and transferred to 400 µl of wash 1 solution, the samples were mixed in wash 1 for 30 s, the beads were collected and transferred to 150 µl of wash 2 solution, the samples were mixed in wash 2 for 30 s, the beads were collected and then dried for 1 min, the beads were transferred to the nuclease treatment plate and mixed for 30 min at 37° C.

For RNA Isolation: RNA samples were treated with a DNase mixture (4 µl DNase+196 µl 1×DNase buffer). After treatment, 500 µl of a rebinding mixture (150 µl binding buffer+350 µl isopropanol) was added to each sample.

For DNA Isolation: DNA samples were treated with an RNase mixture (10 µl RNase A+190 µl nuclease-free water). After treatment, 600 µl of a rebinding mixture (200 µl binding buffer+400 µl isopropanol) was added to each sample.

For either RNA or DNA isolation, the samples were then mixed for 3 min with rebinding reagents, the beads were then collected and transferred to 150 µl of wash 2 solution for 30 s. The wash 2 step was repeated, followed by collection and drying of the beads for 1-2 min.

Elution of RNA: The beads were then transferred to the elution solution and mixed for 4 min at 37° C.

Elution of DNA: The beads were then transferred to the elution solution and mixed for 4 min at ~70 °–80° C.

For either RNA or DNA isolation, the beads were then collected, leaving the purified nucleic acid in the elution buffer. The elution plate (with elution buffer) was removed from the instrument and stored at −20° C.

EXAMPLE 2: Yield and CT Analysis of Isolated Nucleic Acid

Nucleic acid isolated using the protocol of Example 1 was analyzed for yield, and for CT analysis using qPCR, qRT-PCR, and miRNA qRT-PCR.

Yield: The concentration of nucleic acid was measured using a NANODROP™ spectrophotometer on 2 µl of material. The average and standard deviations of the total yield were calculated using the following formula: µg NA=((ng/µl)/1000)*Elution Volume (µl).

qPCR for DNA: Isolated DNA (10 ng/µl) was analyzed using the TAQMAN® Universal PCR Master Mix II, No AmpErase® UNG (Applied Biosystems, PN 4352042) and assays were run in a 7900HT Fast Real-Time PCR System (Applied Biosystems) using the protocol below.

1. 95C 10min
2. 95C 15s  } 40 Cycles
3. 60C 60s

The results were analyzed by performing automatic CT analysis with SDSv2.3 software and export results. Failed reaction results were removed, then the average and standard deviations for each set of triplicate reactions were calculated. Primers for the DNA TAQMAN® assays were: for 18S (Assay ID Hs99999901_s1, SKU 4331182), for RNase P (SKU 4316838), and for TAF9 (Assay ID Rn00788409_s1, SKU 4331182), all from Applied Biosystems.

qRT-PCR for mRNA: Isolated RNA (10 ng/ul) was reverse transcribed using the High Capacity cDNA Reverse Transcription Kit and protocol (Applied Biosystems, PN 4368814) and the 9700 Thermocycler (Applied Biosystems) with the following conditions: 25° C. for 10 min; 37° C. for 2 hr; 85° C. for 5 s; and 4° C. until use. Once the RT reactions were complete, they were placed on ice. qPCR reactions for resultant cDNA were carried out and results analyzed as for DNA above. Primers for the mRNA target TAQMAN® assays were: for ENO1 (Assay ID Hs00361415_m1, SKU 4331182; and Assay ID Rn00820597_g1, SKU 4331182) and for ACTB (Assay ID Hs00357333_g1, SKU 4331182; and Assay ID Rn00667869_m1, SKU 4331182), all from Applied Biosystems.

qRT-PCR for miRNA: Isolated RNA (5 ng/µl) was reverse transcribed using the TAQMAN® MicroRNA RT Kit (Applied Biosystems) and gene specific RT primers in a 9700 thermocycler and the following cycles were used: 4° C. for 5 min, 16° C. for 30 min, 42° C. for 30 min, 85° C. for 5 min, and 4° C. until use. Once RT reactions were complete, they were placed on ice. qPCR reactions were carried out and results analyzed as for DNA or cDNA above. Primers for miRNA target TAQMAN® assays were: for miR16 (Assay ID 00391, SKU 4427975) and for Let7a (Assay ID 000377, SKU 4427975), all from Applied Biosystems.

EXAMPLE 3: Yield of RNA Using Direct Isolation from Clinical FFPE Samples in the Presence of Various Additives RNA was isolated from an about 18 yr old sample detailed in Example 1. Duplicate isolations were performed for each condition using the protocol in Example 1 with the following changes: 100 µl of digestion buffer was used, the digestion buffer contained 4M urea instead of 0.5M, and 100 µl of each additive was used (~50% in the sample). A shorter digestion time was used: 60° C. for 20 min followed by 80° C. for 15 min. Ethanol (200 µl) was used for the initial binding instead of 420 µl isopropanol. Binding buffer (100 µl) contained sodium acetate and 100 µl was used. Wash volumes were: 800 µl for wash 1 and 450 µl for wash 2. Further, 25 µl of beads were used instead of 20 µl. Average yield of RNA (ng) is provided in FIG. 1 for each sample preparation. The FIG. 1 x-axis designations depict the nucleic acid isolation method tested as follows a=the additive was poly(ethylene glycol)-block-poly(propylene glycol)-block-poly(ethylene glycol), $M_n$ 1100;
b=the additive was poly(ethylene glycol) $M_n$ 200;
c=the additive was poly(ethylene glycol) $M_n$ 400;
d=the additive was poly(ethylene glycol) $M_n$ 1000;
e=the additive was BRIJ® 30;
f=the additive was BRIJ® 35P;
g=the additive was BRIJ® 56;
h=the additive was BRIJ® 76;
x=control isolation using standard xylene/ethanol deparaffinization, the RECOVERALL™ Total Nucleic Acid Isolation Kit for FFPE (Applied Biosystems, cat#AM1975).

As shown in FIG. 1, to different degrees, RNA can be successfully isolated from FFPE samples without an upfront organic solvent deparaffinization. The poly(alkylene glycol)-related additives (including the block copolymer) provided a higher yield of RNA than did the BRIJ® detergents. Therefore, nucleic acid isolated from FFPE samples using the poly(alkylene glycol) and block copolymer-related additives was studied further for functionality in qPCR as provided below in Example 4.

EXAMPLE 4: Yield and qPCR Functionality of RNA Using Direct Isolation from Clinical FFPE Samples in the Presence of Various Additives RNA was isolated from an about 18 yr old human clinical FFPE block (Example 1). Duplicate isolations were performed in the presence of each additive a, b, c, and d (above) using the same protocol as for Example 3 with the following changes: Samples were digested in 1.5 ml tubes in a thermomixer, then transferred to a 96-well plate for RNA isolation.

Figure 2A:
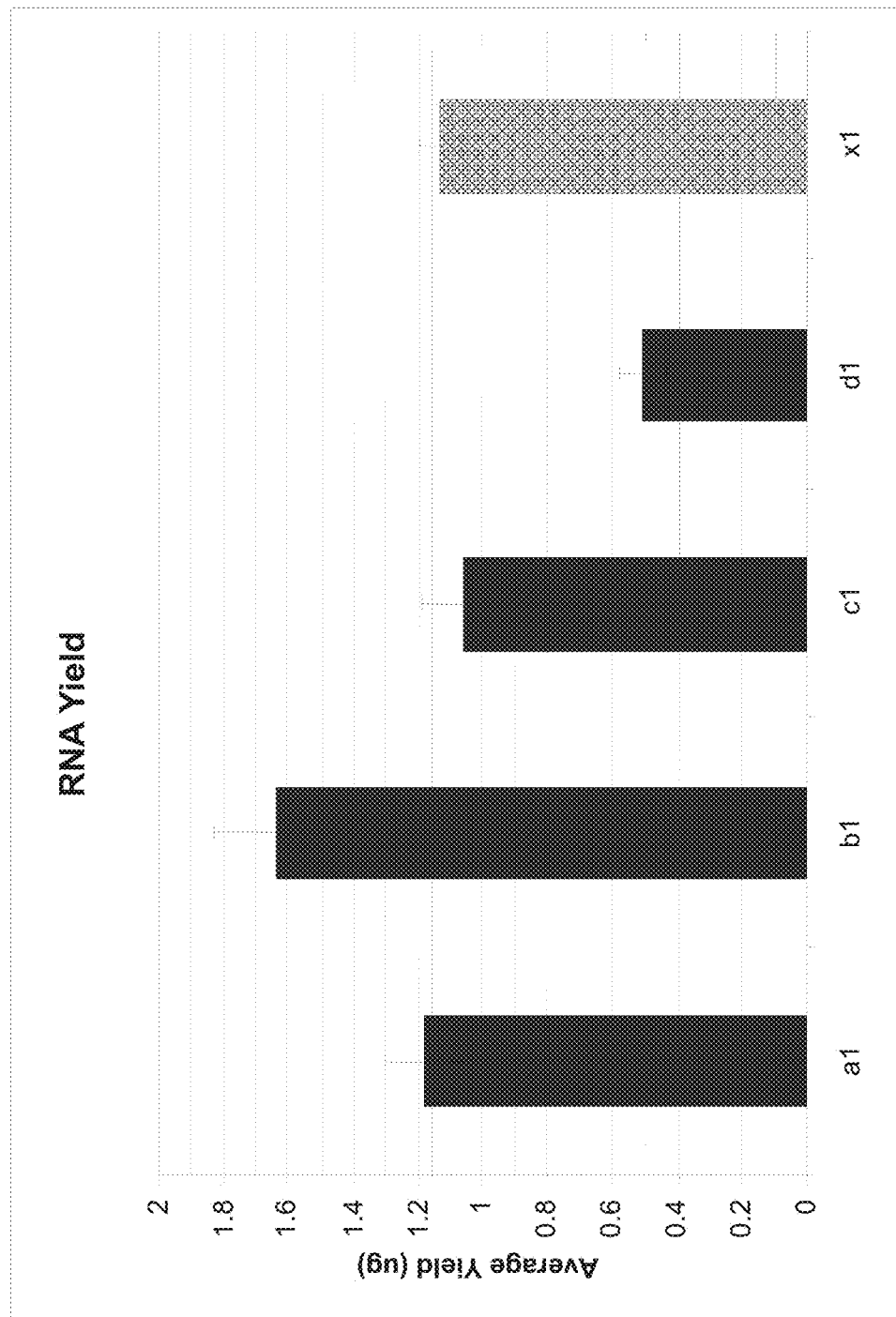

FIG. 2A provides yield results from isolation protocols where the x-axis designations depict the nucleic acid isolation method tested as follows
  a1=the additive was poly(ethylene glycol)-block-poly(propylene glycol)-block-poly(ethylene glycol), $M_n$ 1100;
  b1=the additive was poly(ethylene glycol) $M_n$ 200;
  c1=the additive was poly(ethylene glycol) $M_n$ 400;
  d1=the additive was poly(ethylene glycol) $M_n$ 1000;
  x=control isolation using standard xylene/ethanol deparaffinization, the RECOVERALL™ Total Nucleic Acid Isolation Kit for FFPE (Applied Biosystems, cat#AM1975).

Use of the poly(ethylene glycol) additive having an $M_n$ of 1000 (d1, FIG. 2A) in direct isolation of RNA from FFPE samples provided a yield of less than one half the yield of isolation procedures using the block copolymer (a1, FIG. 2A), other PEGs having a lower number average molecular weight (b1 or c1, FIG. 2A), and the control procedure (x1, FIG. 2A).

FIG. 2B provides the results for analyzing RNA, isolated using the additives as cited above, for qRT-PCR functionality using mRNA targets ENO1 and ACTB. The FIG. 2B x-axis designations for a1, b1, c1, d1, and x1 are as for FIG. 2A. While mRNA was detectable for both targets using isolation procedures with each of the additives, the isolation procedure containing additive a1, i.e., the block copolymer, provided a CT comparable to that of the control isolation procedure x1.

Figure 2C:
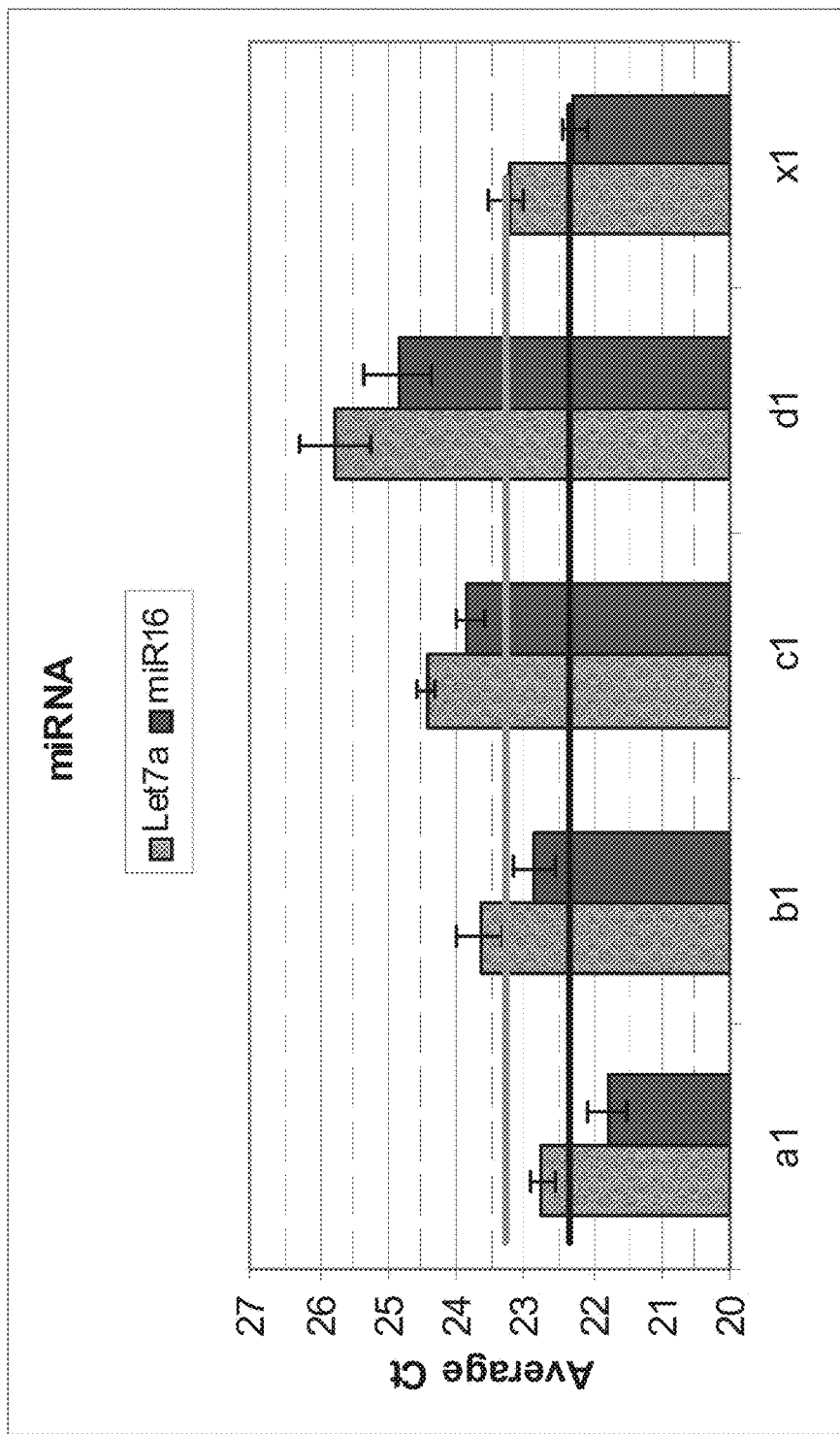

FIG. 2C provides the results for analyzing RNA, isolated using the additives as cited above, for qRT-PCR functionality using miRNA targets Let7a and miR16. The FIG. 2C x-axis designations for a1, b1, c1, d1, and x1 are as for FIG. 2A and FIG. 2B. MicroRNA was detectable for both targets using isolation procedures with each of the additives. The isolation procedure containing the block copolymer additive a1 provided CT results that were better than the control procedure.

EXAMPLE 5: Alkylene Glycol, Poly(Alkylene Glycol) and Block Copolymers in Direct Isolation of Nucleic Acids from Clinical FFPE Samples Further alkylene glycol, poly(alkylene glycol) and block copolymer additives were studied in the direct isolation of RNA and DNA from two different clinical FFPE tissue blocks and resultant RNA and DNA were analyzed for yield and for functionality in qPCR. Duplicate isolations were performed for each additive using the general protocol and reagents of Example 3 with the following changes: 100 μl of digestion buffer was used, and 20 μl of each additive was used (additives are at ~15% in the digestion). Digestion time was the same for both RNA and DNA isolation: 60° C. for 45 min followed by 80° C. for 30 min. Binding buffer volume was 135 μl and the isopropanol volume was 270 μl for the initial binding. Wash volumes were: 800 μl for wash 1 and 450 μl for wash 2. A volume of 25 μl of beads was used for isolation instead of 20 μl.

Figure 3A:
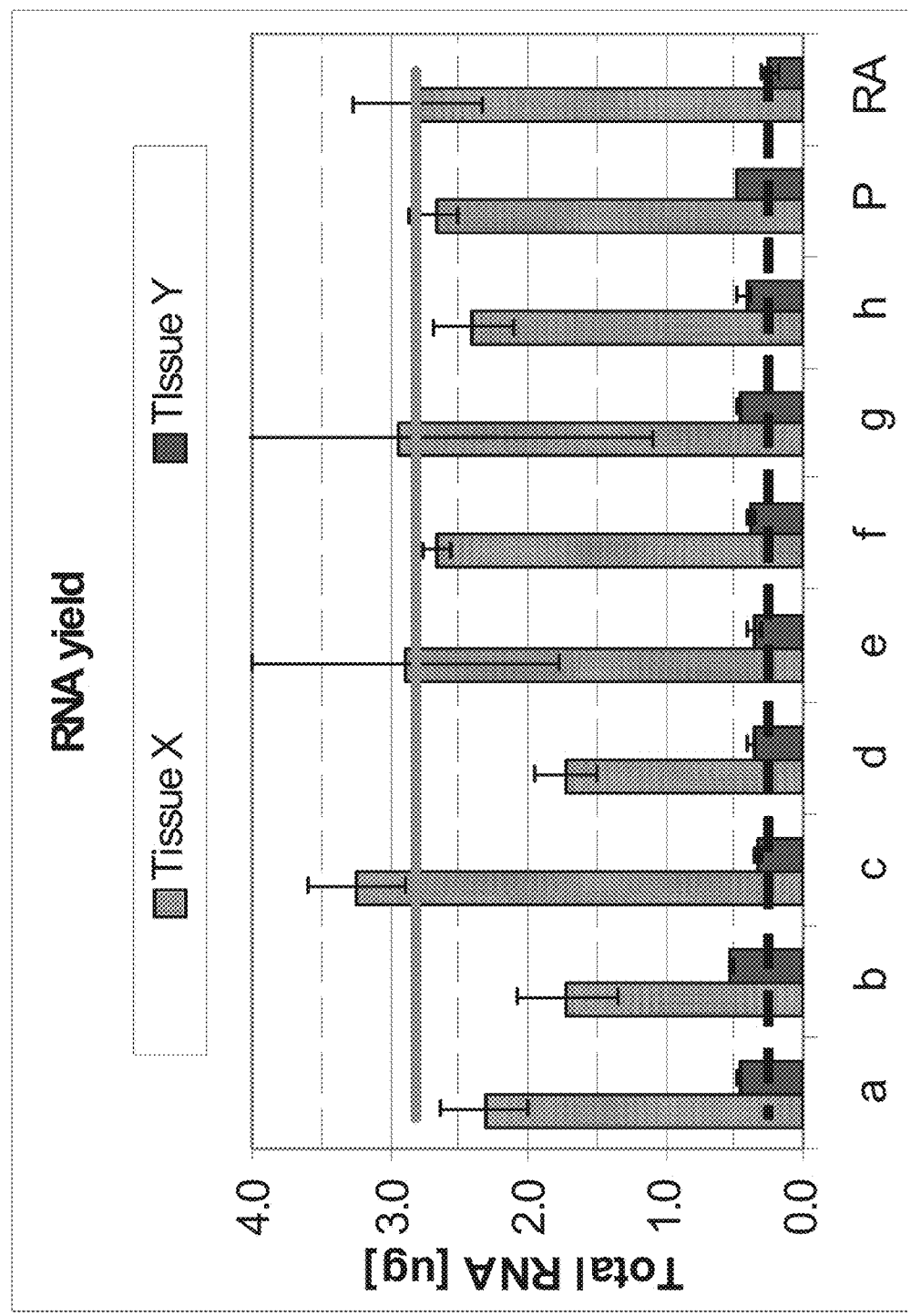
Figure 3B:
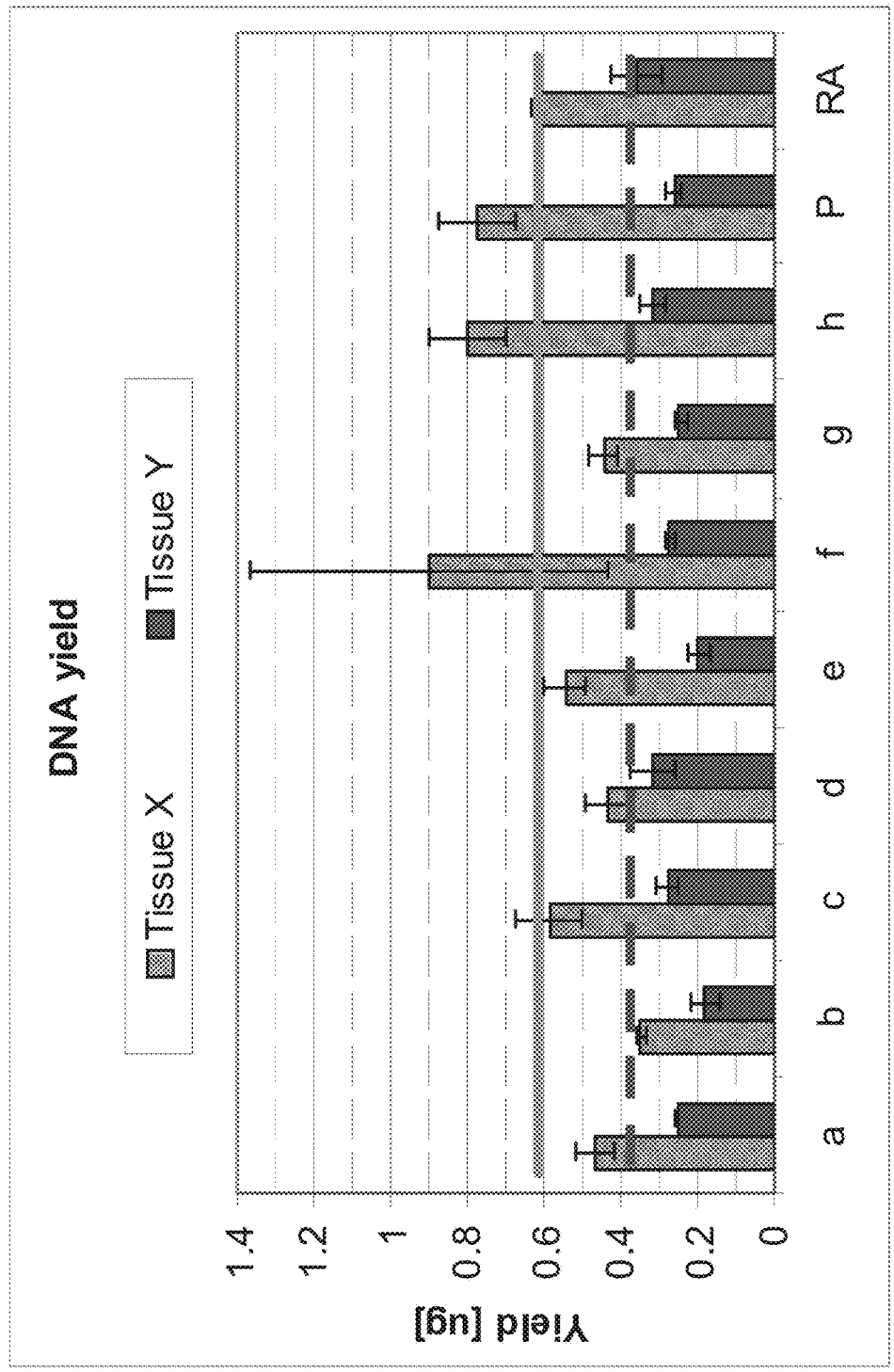
Figure 3E:
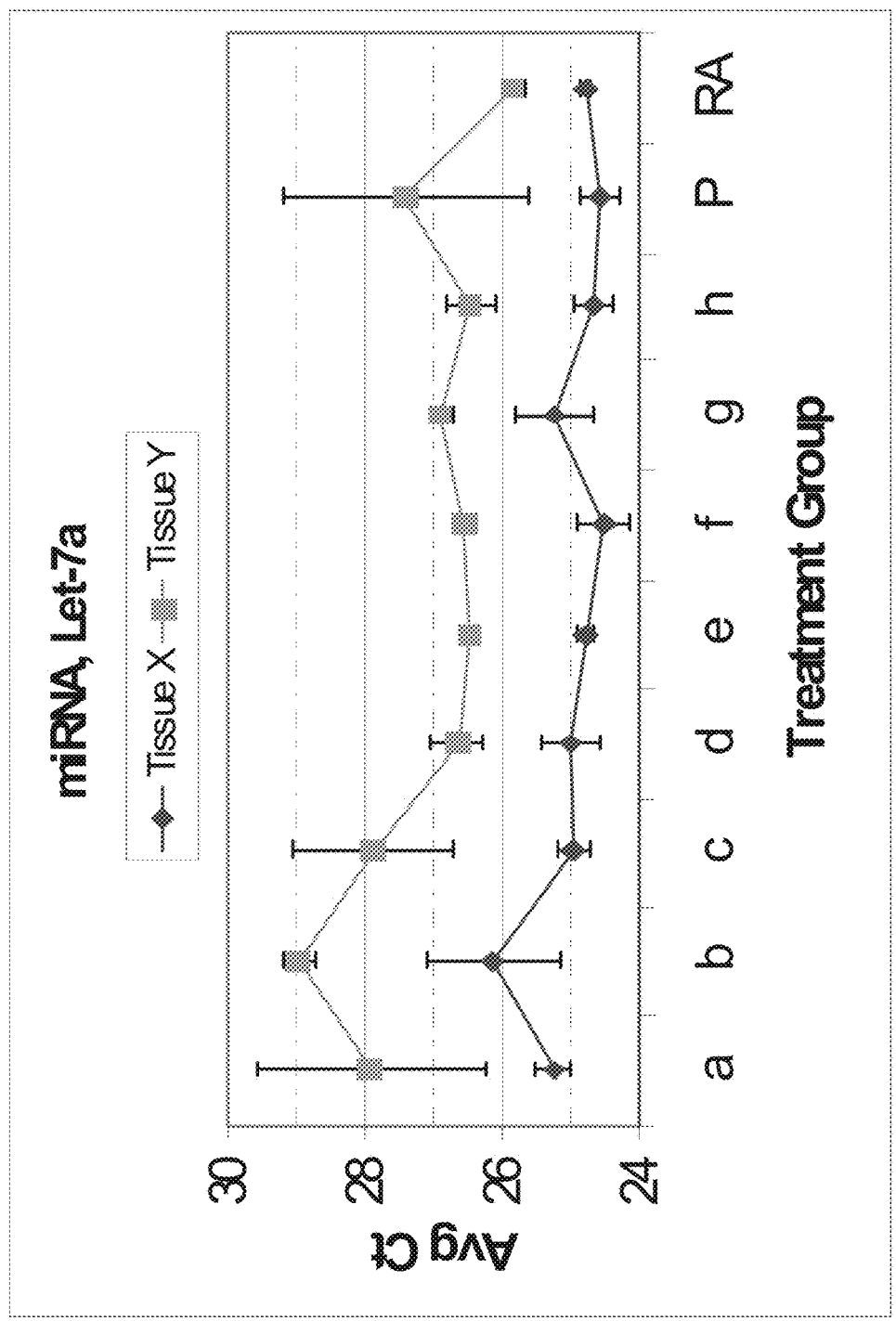

FIG. 3A-FIG. 3E show the results of the studies as follows:
  FIG. 3A, RNA yield;
  FIG. 3B, DNA yield;
  FIG. 3C, qRT-PCR of the mRNA target ACTB;
  FIG. 3D, qPCR of the DNA target RNase P; and
  FIG. 3E, qRT-PCR of the miRNA target Let-7a.
The x-axis designations for FIG. 3A-FIG. 3E depict the additive present during isolation as follows
  a=Propylene glycol $M_n$ 76.1;
  b=Poly(propylene glycol) $M_n$ 425;
  c=Poly(ethylene glycol)-block-poly(propylene glycol)-block-poly(ethylene glycol) $M_n$ 1900;
  d=Poly(ethylene glycol)-block-poly(propylene glycol)-block-poly(ethylene glycol) $M_n$ 2000;
  e=Poly(ethylene glycol)-block-poly(ethylene glycol)-block-poly(propylene glycol) $M_n$ 2000;
  f=Poly(propylene glycol) $M_n$ 1000;
  g=Poly(propylene glycol) $M_n$ 400;
  h=Poly(propylene glycol) $M_n$ 1200;
  P=poly(ethylene glycol)-block-poly(propylene glycol)-block-poly(ethylene glycol) $M_n$ 1100; (this is the same additive as for "a" of FIG. 1 and as for "a1" of FIG. 2A-FIG. 2C);
  RA=control isolation using standard xylene/ethanol deparaffinization, the RECOVERALL™ Total Nucleic Acid Isolation Kit for FFPE (Applied Biosystems, cat#AM1975).

"As shown in FIG. 3A-FIG. 3E, for both DNA and RNA, all additives showed similar yield and function compared to each other and the control. Additive "b" appears to be somewhat of an exception with regard to functionality in the DNA assay.

One of the key benefits of using the additive (aside from removal of the separate deparaffinization step) is the significant reduction of digestion time needed for DNA isolation. The majority of existing protocols for DNA isolation from FFPE samples (such as the RECOVERALL™ kit) state an overnight proteinase K digestion. With the methods provided herein, the time of digestion for isolation of DNA is shortened and is equal to the digestion time for isolation of RNA.

Further conditions for isolation of RNA and DNA from two ~18 yr old samples demonstrated that an amount of 20 μl of beads was also effective in the protocols with additives present.

The isolation protocols with additives were also tested on different tissues as follows: RNA and DNA were isolated separately and from several different tissue types: four 18 yr old unidentified human samples and three 6 month old rat tissues (brain, kidney, and liver). Triplicate isolations were performed using the general protocol and reagents in Example 1. Yields were equivalent or better for all samples compared to the xylene-treated control. Equal mass input of the samples into qRT-PCR or qPCR was analyzed for miRNA, mRNA, and DNA TAQMAN® assays. Both RNA and DNA samples showed similar or equivalent CT values compared to the xylene-treated control for miRNA, mRNA, and DNA targets. In summary, presence of additives provided for isolation of RNA and DNA in similar yield and function to the xylene-treated control. A separate step of deparaffinization, therefore, is not needed for purification of nucleic acid from FFPE samples.

Different types of magnetic beads were examined for isolation of RNA in the protocols presented herein. NANOMAG-D® plain beads from Micromod (Rostock-Warnemuende, Germany) and DYNABEADS® MYONE™ silane magnetic beads (Invitrogen) were compared and found to perform comparably for detection of mRNA targets. However, results using the NANOMAG-D® plain beads demonstrated somewhat better functionality for miRNA targets than using the DYNABEADS® MYONE™ silane magnetic beads. Both types of beads provided comparable A260/280 ratios; however, use of the DYNABEADS® MYONE™ silane magnetic beads provided a strong A230 nm absorbance for isolated RNA, thereby providing lower A260/230 ratios than that provided by the NANOMAG-D® plain beads.

Each embodiment disclosed herein may be used or otherwise combined with any of the other embodiments disclosed. Any element of any embodiment may be used in any embodiment. Although the invention has been described with reference to specific embodiments, it will be understood by those skilled in the art that various changes may be made and equivalents may be substituted for elements thereof without departing from the true spirit and scope of the invention. In addition, modification may be made without departing from the essential teachings of the invention.

What is claimed is:

1. A method for isolation of nucleic acid from a paraffin-embedded biological sample comprising: contacting the paraffin-embedded biological sample with
   a) a thermostable protease, and
   b) an additive comprising
      i) an alkylene glycol having a number average molecular weight (Mn) of 76 to 2900,
      ii) a poly(alkylene glycol) having an average Mn of 76 to 2900,
      iii) a block copolymer of a poly(alkylene glycol) having an average Mn of 76 to 2900,
      iv) a salt of i), ii) or iii), or
      v) any combination of i), ii) iii), or iv)
under conditions to produce an emulsified digest; and isolating nucleic acid from the emulsified digest wherein the paraffin-embedded biological sample comprises an embedding medium comprising paraffin and no separate step of removing the embedding medium is used during the method for isolation of nucleic acid from the paraffin-embedded biological sample.

2. The method of claim 1, wherein the additive comprises an alkylene glycol, or a combination of different alkylene glycols, or a salt of the alkylene glycol or the combination of different alkylene glycols or combination thereof or wherein the additive comprises a poly(alkylene glycol), or a combination of different poly(alkylene glycols), or a salt of the polyalkylene glycol or the combination of different polyalkylene glycols or combination thereof.

3. The method of claim 2, wherein the alkylene glycol comprises propylene glycol, or a salt of the propylene glycol or combination thereof.

4. The method of claim 2, wherein the poly(alkylene glycol) comprises poly(propylene glycol), or a salt of the poly(propylene glycol) or combination thereof or wherein the poly(alkylene glycol) comprises poly(ethylene glycol), or a salt of the poly(ethylene glycol) or combination thereof.

5. The method of claim 1, wherein the additive comprises a block copolymer, or a salt of the block copolymer or derivative of the block copolymer or combination thereof.

6. The method of claim 5, wherein the block copolymer comprises poly(propylene glycol)-block-poly(ethylene glycol)-block-poly(propylene glycol), poly(ethylene glycol)-block-poly(propylene glycol)-block-poly (ethylene glycol), or a salt of the poly(propylene glycol)-block-poly(ethylene glycol)-block-poly(propylene glycol) or poly(ethylene glycol)-block-poly(propylene glycol)-block-poly (ethylene glycol) or combination thereof.

7. The method of claim 1, wherein the paraffin-embedded sample is a formalin-fixed paraffin embedded (FFPE) tissue sample.

8. The method of claim 1 wherein the conditions to produce the emulsified digest include heating, optionally in the presence of a mild chaotrope to produce the emulsified digest, or the use of a mild chaotrope during the contacting step.

9. The method of claim 1, wherein said isolating nucleic acid comprises:
   contacting the emulsified digest with a solid support under conditions wherein the nucleic acid binds to the solid support; and
   eluting the nucleic acid from the solid support thereby providing eluted nucleic acid.

10. The method of claim 9, wherein the nucleic acid is DNA and isolating the DNA comprises:
    contacting the eluted nucleic acid with a ribonuclease thereby forming a ribonuclease digest;
    contacting the ribonuclease digest with a solid support under conditions wherein the DNA binds to the solid support; and
    eluting the DNA from the solid support.

11. The method of claim 9, wherein the nucleic acid is RNA and isolating the RNA comprises:
    contacting the eluted nucleic acid with a deoxyribonuclease thereby forming a deoxyribonuclease digest;
    contacting the deoxyribonuclease digest with a solid support under conditions wherein the RNA binds to the solid support; and
    eluting the RNA from the solid support.

* * * * *